(12) United States Patent
Mejia Oneto et al.

(10) Patent No.: US 12,194,100 B2
(45) Date of Patent: Jan. 14, 2025

(54) PROCESSES FOR PREPARING FUNCTIONALIZED CYCLOOCTENES

(71) Applicant: Tambo, Inc., San Francisco, CA (US)

(72) Inventors: Jose M. Mejia Oneto, San Francisco, CA (US); Nathan Yee, San Francisco, CA (US); Jochem Theodoor Van Herpt, Groningen (NL); Chun-Min Zeng, Cranbury, NJ (US); Da-Ming Gou, Cranbury, NJ (US); Maksim Royzen, Albany, NY (US)

(73) Assignees: Tambo, Inc., San Francisco, CA (US); The Research Foundation of the State University of New York, Albany, NY (US)

( * ) Notice: Subject to any disclaimer, the term of this patent is extended or adjusted under 35 U.S.C. 154(b) by 805 days.

(21) Appl. No.: 17/284,434

(22) PCT Filed: Oct. 10, 2019

(86) PCT No.: PCT/US2019/055707
§ 371 (c)(1),
(2) Date: Apr. 9, 2021

(87) PCT Pub. No.: WO2020/077140
PCT Pub. Date: Apr. 16, 2020

(65) Prior Publication Data
US 2021/0346502 A1  Nov. 11, 2021

Related U.S. Application Data

(60) Provisional application No. 62/744,041, filed on Oct. 10, 2018.

(51) Int. Cl.
| | |
|---|---|
| *C07C 51/47* | (2006.01) |
| *A61K 31/704* | (2006.01) |
| *A61K 38/07* | (2006.01) |
| *A61K 38/14* | (2006.01) |
| *A61K 38/15* | (2006.01) |
| *A61K 47/14* | (2017.01) |
| *C07C 61/26* | (2006.01) |
| *C07C 62/30* | (2006.01) |
| *C07C 62/32* | (2006.01) |
| *C07C 67/327* | (2006.01) |
| *C07D 207/46* | (2006.01) |
| *C07D 311/94* | (2006.01) |
| *C07D 493/08* | (2006.01) |

(52) U.S. Cl.
CPC ............ *A61K 47/14* (2013.01); *A61K 31/704* (2013.01); *A61K 38/07* (2013.01); *A61K 38/14* (2013.01); *A61K 38/15* (2013.01); *C07C 51/47* (2013.01); *C07C 61/26* (2013.01); *C07C 62/30* (2013.01); *C07C 62/32* (2013.01); *C07C 67/327* (2013.01); *C07D 207/46* (2013.01); *C07D 311/94* (2013.01); *C07D 493/08* (2013.01); *C07C 2601/18* (2017.05)

(58) Field of Classification Search
CPC .......... C07C 61/26; C07C 62/30; C07C 62/32; C07C 67/327
See application file for complete search history.

(56) References Cited

U.S. PATENT DOCUMENTS

| | | |
|---|---|---|
| 4,166,916 A | 9/1979 | Sanders et al. |
| 10,130,711 B2 | 11/2018 | Mejia Oneto et al. |
| 10,130,723 B2 | 11/2018 | Mejia Oneto et al. |
| 10,342,882 B2 | 7/2019 | Mejia Oneto et al. |
| 10,806,807 B2 | 10/2020 | Mejia Oneto et al. |
| 10,828,373 B2 | 11/2020 | Mejia Oneto et al. |
| 10,953,098 B2 | 3/2021 | Mejia Oneto et al. |
| 2009/0023916 A1 | 1/2009 | Fox et al. |
| 2014/0093450 A1 | 4/2014 | Robillard et al. |
| 2015/0344514 A1 | 12/2015 | Robillard et al. |
| 2020/0354096 A1 | 11/2020 | Tekemura et al. |

FOREIGN PATENT DOCUMENTS

| | | | |
|---|---|---|---|
| WO | WO2012/156918 A1 | 11/2012 | |
| WO | WO2014/081299 A1 | 5/2014 | |
| WO | WO2014/081300 A1 | 5/2014 | |
| WO | WO2014/081301 A1 | 5/2014 | |
| WO | WO 2015/139025 | 9/2015 | |
| WO | WO 2017/044983 | 3/2017 | |
| WO | WO-2018187740 A1 * | 10/2018 | ............ A61K 45/06 |
| WO | WO-2019212357 A1 * | 11/2019 | ............ A61K 38/07 |
| WO | WO 2020/077140 | 4/2020 | |

OTHER PUBLICATIONS

Carlson et al., "Supporting Information: Unraveling Tetrazine-Triggered Bioorthogonal Elimination Enables Chemical Tools for Ultrafast Release and Universal Cleavage," Journal of the American Chemical Society, 2018, 68 pages.
Carlson et al., "Unraveling Tetrazine-Triggered Bioorthogonal Elimination Enables Chemical Tools for Ultrafast Release and Universal Cleavage," Journal of the American Chemical Society, 2018, vol. 140, No. 10, pp. 3603-3612.
Extended European Search Report, dated Oct. 12, 2022, regarding Application No. EP19870590.7, 28 pages.
International Search Report and Written Opinion, dated Feb. 10, 2020, regarding International Application No. PCT/US2019/055707, 11 pages.

(Continued)

*Primary Examiner* — Amanda L. Aguirre
(74) *Attorney, Agent, or Firm* — Sheppard Mullin Richter & Hampton LLP

(57) ABSTRACT

The present disclosure relates to processes for preparing functionalized cyclooctenes and the synthetic intermediates prepared thereby.

7 Claims, No Drawings

(56) References Cited

OTHER PUBLICATIONS

Leeman, "Resolutions of Racemates by Crystallization," Thesis, University of Groningen, 2009, URL: https://pure.rug.nl/ws/portalfiles/portal/14648608/thesis.pdf.
Rossin et al., "Supporting Information: Triggered Drug Release from an Antibody-Drug Conjugate Using Fast 'Click-to-Release' Chemistry in Mice," Bioconjugate Chemistry, 2016, 46 pages.
Rossin et al., "Triggered Drug Release from an Antibody-Drug Conjugate Using Fast 'Click-to-Release' Chemistry in Mice," Bioconjugate Chemistry, 2016, vol. 27, No. 7, pp. 1697-1706.
Van Der Gracht et al., "Chemical Control over T-Cell Activation in Vivo Using Deprotection of trans-Cyclooctene-Modified Epitopes," ACS Chemical Biology, 2018, vol. 13, No. 6, pp. 1569-1576.
U.S. Appl. No. 16/603,471, filed Oct. 7, 2019.
International Search Report and Written Opinion, PCT/US2019/055707, dated Oct. 2, 2020, 10 pages.

\* cited by examiner

PROCESSES FOR PREPARING FUNCTIONALIZED CYCLOOCTENES

CROSS REFERENCE TO RELATED APPLICATIONS

This application is the U.S. national stage application of International Application No. PCT/US2019/055707 filed Oct. 10, 2019, which claims the benefit under 35 U.S.C. § 119(e) of U.S. Provisional Application 62/744,041, filed Oct. 10, 2018, each of which is hereby incorporated by reference in its entirety.

GOVERNMENT LICENSE RIGHTS

This invention was made with government support under Grant No. CA228997 awarded by the National Institutes of Health. The government has certain rights in this invention.

FIELD

The present disclosure relates to processes for preparing functionalized cyclooctenes and the synthetic intermediates prepared thereby.

BACKGROUND

Bioorthogonal conjugation or click reactions are selective and orthogonal (non-interacting with) functionalities found in biological systems, and have found use in various applications in the fields of chemistry, chemical biology, molecular diagnostics, and medicine, where they can be used to facilitate the selective manipulation of molecules, cells, particles and surfaces, and the tagging and tracking of biomolecules in vitro and in vivo. These reactions include the Staudinger ligation, the azide-cyclooctyne cycloaddition, and the inverse-electron-demand Diels-Alder reaction. The present disclosure provides methods for preparing functionalized payload compositions for use in such reactions, which have improved aqueous solubility, for delivering therapeutic agents to a subject.

SUMMARY

The functionalized payloads according to the present disclosure have improved aqueous solubility compared with payloads linked to an unsubstituted cyclooctene, and therefore are more easily formulated and administered.

Provided herein is a process of preparing a compound of formula I, or a salt thereof:

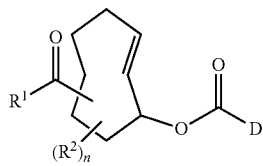

wherein
R$^1$ is selected from the group consisting of —OR$^4$, optionally substituted heterocyclyl, and an amino acid moiety;
n is 0, 1, 2, 3 or 4;
each R$^2$ is independently C$_{1-4}$alkyl, C$_{1-4}$haloalkyl, and C$_{1-4}$alkoxy;
D is a payload moiety; and
R$^4$ is hydrogen or C$_{1-4}$alkyl;
comprising contacting a compound of formula II:

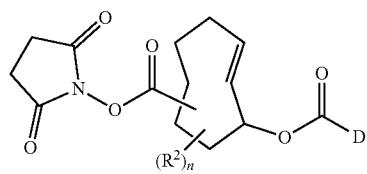

with HO—R$^4$, an optionally substituted heterocyclyl or an amino acid moiety, or a salt thereof, and a compound of formula III:

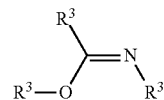

wherein each R$^3$ is independently C$_{1-4}$alkyl, in an organic solvent in the presence of a base. Also provided is a process of preparing a compound of formula X, or a salt thereof:

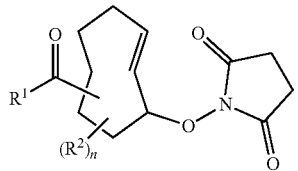

wherein
R$^1$ is selected from the group consisting of —OR$^4$, optionally substituted heterocyclyl, and an amino acid moiety;
n is 0, 1, 2, 3 or 4;
each R$^2$ is independently C$_{1-4}$alkyl, C$_{1-4}$haloalkyl, and C$_{1-4}$alkoxy; and R$^4$ is hydrogen or C$_{1-4}$alkyl;
comprising contacting a compound of formula IV:

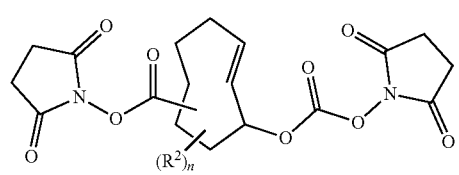

with HO—R⁴, an optionally substituted heterocyclyl or an amino acid moiety, or a salt thereof, and a compound of formula III:

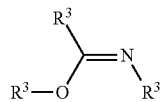

III wherein each R³ is independently $C_{1-4}$alkyl, in an organic solvent in the presence of a base.

Also provided is a process of preparing a compound of formula I, or a salt thereof:

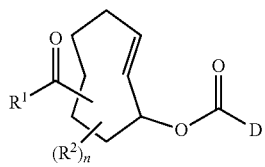

I wherein
R¹ is selected from the group consisting of —OR⁴, optionally substituted heterocyclyl, and an amino acid moiety;
n is 0, 1, 2, 3 or 4;
each R² is independently $C_{1-4}$alkyl, $C_{1-4}$haloalkyl, and $C_{1-4}$alkoxy;
D is a payload moiety; and
R⁴ is hydrogen or $C_{1-4}$alkyl;
comprising contacting a compound of formula X, or a salt thereof:

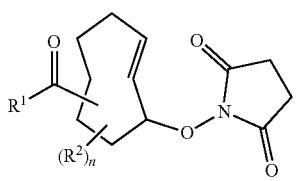

X with a payload moiety, or a salt thereof, in an organic solvent in the presence of a base.

Also provided is a process of preparing a composition comprising a compound of formula IV, or a salt thereof:

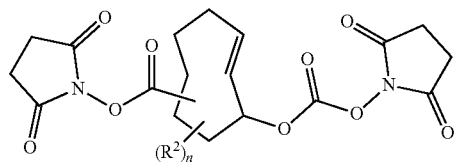

IV wherein
n is 0, 1, 2, 3, or 4; and
each R² independently hydrogen or $C_{1-4}$alkyl;
comprising contacting one equivalent of a compound of formula V, or a salt thereof:

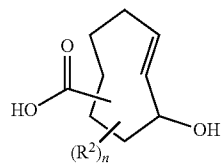

V with 3-5 equivalents of N,N'-disuccinimidylcarbonate in 15-25 volumes of an anhydrous organic solvent in the presence of a base at a temperature from 15-30° C. for 5-10 hours.

Also provided is a process for resolving a composition comprising one or more stereoisomers of a compound of formula VI, or a salt thereof:

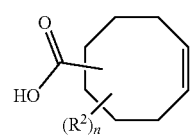

VI wherein
n is 0, 1, 2, 3, or 4;
each R² is independently $C_{1-4}$alkyl, $C_{1-4}$haloalkyl, and $C_{1-4}$alkoxy;
comprising the steps of:
(a) contacting a composition comprising one or more stereoisomers of formula VI with a chiral base to provide a chiral salt of the compound of formula VI;
(b) cooling the composition of step (a);
(c) isolating the chiral salt of the compound of formula VI; and
(d) hydrolyzing the chiral salt of the compound of formula VI to provide the enantiomerically enriched composition comprising a compound of formula VI, or a salt thereof.

In certain embodiments, the process comprises repeating steps (b) and (c) prior to step (d).

Also provided is a process for the preparation of an enantiomerically enriched composition comprising a compound of formula VII, or a salt thereof:

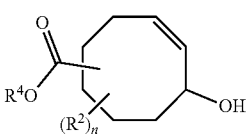

VII wherein
n is 0, 1, 2, 3 or 4;
each R² is independently $C_{1-4}$alkyl, $C_{1-4}$haloalkyl, and $C_{1-4}$alkoxy; and
R⁴ is independently hydrogen or $C_{1-4}$alkyl;
comprising sequentially contacting an enantiomerically enriched composition of a compound of formula VI, or a salt thereof:

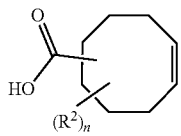

with: (i) a solution comprising KI and $I_2$, (ii) a base, and (iii) a hydrolyzing composition comprising a base and a compound of formula $R^4$—OH, to provide the enantiomerically enriched composition of a compound of formula VII, or a salt thereof.

Also provided is a process for resolving a composition comprising one or more stereoisomers of a compound of formula VIIA, or a salt thereof:

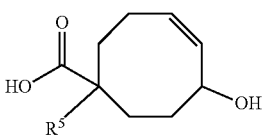

wherein
$R^5$ is hydrogen or $C_{1-4}$alkyl, comprising the steps of:
(a) contacting a composition comprising one or more stereoisomers of formula VIIA with a chiral base to provide a chiral salt of the compound of formula VIIA;
(b) cooling the composition of step (a);
(c) isolating the chiral salt of the compound of formula VIIA; and
(d) hydrolyzing the chiral salt of the compound of formula VIIA to provide the enantiomerically enriched composition comprising a compound of formula VIIA, or a salt thereof.

Also provided is a process for the preparation of an enantiomerically enriched composition comprising a compound of formula VB, or a salt thereof:

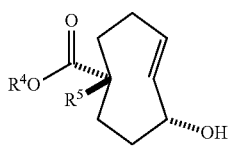

wherein
$R^4$ is hydrogen or $C_{1-4}$alkyl; and
$R^5$ is hydrogen or $C_{1-4}$alkyl;
comprising isomerizing an enantiomerically enriched composition of a compound of formula VIIB, or a salt thereof:

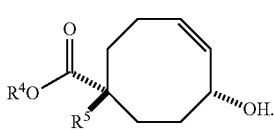

Also provided is an enantiomerically enriched composition comprising a compound selected from Table 1, or a salt thereof.

DETAILED DESCRIPTION

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B . . . or N including any one element alone or in combination with one or more of the other elements which may also include, in combination, additional elements not listed.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3rd Edition, Cambridge University Press, Cambridge, 1987: the entire contents of each of which are incorporated herein by reference.

The term "enantiomerically enriched" as used herein, refers to a composition of a chiral substance whose enantiomeric ratio is greater than 50:50, but less than 100:0. In certain embodiments, the enantiomerically enriched composition has a % ee of greater than about 25%, or greater than about 30%, or greater than about 35%, or greater than about 40%, or about 45%, or about 50%, or about 55%, or greater than about 60%, or greater than about 65%, or greater than about 70%, or greater than about 75%, or greater than about 80%, or greater than about 85%, or greater than about 90%, or greater than about 95%, or greater than about 97%, or greater than about 99%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or about 97%, or about 99%, or about 100.

The term "alkyl" as used herein, means a straight or branched, saturated hydrocarbon chain containing from 1 to 30 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkenyl" as used herein, means a hydrocarbon chain containing from 2 to 30 carbon atoms with at least one carbon-carbon double bond. The alkenyl group may be substituted or unsubstituted. For example, the alkenyl group may be substituted with an aryl group, such as a phenyl.

The term "alkynyl," as used herein, refers to straight or branched monovalent hydrocarbyl groups having from 2 to 30 carbon atoms, such as 2 to 20, or 2 to 10 carbon atoms and having at least 1 site of triple bond unsaturation. The term "alkyne" also includes non-aromatic cycloalkyl groups of from 5 to 20 carbon atoms, such as from 5 to 10 carbon atoms, having single or multiple rings and having at least one triple bond. Examples of such alkynyl groups include, but are not limited to acetylenyl (—C≡CH), and propargyl (—CH$_2$C≡CH), and cycloalkynyl moieties, such as, but not limited to, substituted or unsubstituted cyclooctyne moieties.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 30 carbon atoms, for example, of 2 to 10 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl" also includes carbocyclic ring systems in which a cycloalkyl group is appended to the parent molecular moiety and is fused to an aryl group as defined herein, a heteroaryl group as defined herein, or a heterocycle as defined herein.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include, but are not limited to, cyclopentenyl, cyclohexenyl or cycloheptenyl.

The term "cyclooctene" as used herein, refers to a substituted or unsubstituted non-aromatic cyclic alkyl group of 8 carbon atoms, having a single ring with a double bond. Examples of such cyclooctene groups include, but are not limited to, substituted or unsubstituted trans-cyclooctene (TCO).

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4 (1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl. 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1 3,7]decane), and oxaadamantane (2-oxatricyclo[3.3.1.1 3,7]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

The term "hydroxyalkyl" as used herein, means an alkyl group, as defined herein, in which one, two, three, four, five, six, seven or eight hydrogen atoms are replaced by a hydroxyl group.

In some instances, the number of carbon atoms in a hydrocarbyl substituent (e.g., alkyl or cycloalkyl) is indicated by the prefix "$C_x$—$C_y$—" or "$C_{x\text{-}y}$," wherein x is the minimum and y is the maximum number of carbon atoms in the substituent. Thus, for example, "$C_1$-$C_3$-alkyl" and "$C_{1\text{-}3}$ alkyl" refer to an alkyl substituent containing from 1 to 3 carbon atoms. The two conventions "$C_x$-$C_y$-" and "$C_{x\text{-}y}$" are used interchangeably and have the same meaning.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "therapeutic agent" refers to an agent capable of treating and/or ameliorating a condition or disease, or one or more symptoms thereof, in a subject. Therapeutic agents of the present disclosure also include prodrug forms of therapeutic agents.

The term "diagnostic agent" refers to agents that assist in diagnosing conditions or diseases. Representative diagnostic agents include imaging agents such as paramagnetic agents, optical probes, radionuclides, and the like. Paramagnetic agents are imaging agents that are magnetic under an externally applied field. Examples of paramagnetic agents include, but are not limited to, iron particles including iron nanoparticles and iron microparticles. Optical probes are fluorescent compounds that can be detected by excitation at one wavelength of radiation and detection at a second, different, wavelength of radiation. Optical probes of the present disclosure include, but are not limited to, Cy5.5, Alexa 680, Cy5, DiD (1,1'-dioctadecyl-3,3,3,3'-tetramethylindodicarbocyanine perchlorate) and DiR (1,1'-dioctadecyl-3,3,3,3'-tetramethylindotricarbocyanine iodide). Other optical probes include quantum dots. Radionuclides are elements that undergo detectable radioactive decay. Radionuclides useful in embodiments of the present disclosure include, but are not limited to, $^{3}H$, $^{11}C$, $^{13}N$, $^{18}F$, $^{19}F$, $^{60}Co$, $^{64}Cu$, $^{67}Cu$, $^{68}Ga$, $^{82}Rb$, $^{90}Sr$, $^{90}Y$, $^{99}Tc$, $^{99m}Tc$, $^{111}In$, $^{123}I$, $^{124}I$, $^{125}I$, $^{129}I$, $^{131}I$, $^{137}Cs$, $^{177}Lu$, $^{186}Re$, $^{188}Re$, $^{211}At$, Rn, Ra, Th, U, Pu and $^{241}Am$.

The term "contacting" or "contact" refers to the process of bringing into contact at least two distinct species such that they can interact with each other, such as in a non-covalent or covalent binding interaction or binding reaction. It should be appreciated, however, the resulting complex or reaction product can be produced directly from an interaction or a reaction between the added reagents or from an intermediate from one or more of the added reagents or moieties, which can be produced in the contacting mixture.

The term "leaving group" refers to an atom (or a group of atoms) with electron withdrawing ability that can be displaced as a stable species, taking with it the bonding electrons. Examples of suitable leaving groups include halides (e.g., Br, Cl, I), sulfonate esters (e.g., triflate, mesylate, tosylate, and brosylate), and nitrophenols.

The term "physiological conditions" is meant to encompass those conditions compatible with living cells, e.g., predominantly aqueous conditions of a temperature, pH, salinity, etc. that are compatible with living cells.

The term "chiral base" is meant to encompass a chiral compound having at least one stereocenter and at least one nitrogen atom. The chiral base can be synthesized using methods known in the art or purchased from commercial sources (e.g., Sigma Aldrich). Exemplary chiral bases include, but are not limited to, L-(−)-α-Amino-ε-caprolactam hydrochloride, (R)-(−)-1-Amino-2-propanol, (S)-(+)-1-Amino-2-propanol, L-Aspartic acid, cis-(1S,2R)-(−)-2-(Benzylamino)cyclohexane methanol, (S)—N-Benzyl-1-(1-naphthyl)ethylamine hydrochloride, (−)-1,4-Bis-O-(4-chlorobenzyl)-L-threitol, (1R,2R)-1,2-Bis(2-hydroxyphenyl)ethylenediamine, (1S,2S)-1,2-Bis(2-hydroxyphenyl)ethylenediamine, (+)-Bis[(R)-1-phenylethyl]amine hydrochloride, N,N-Bis[(S)-(−)-1-phenylethyl]phthalamic acid, (R)-(+)-1-(4-Bromophenyl) ethylamine, (S)-(−)-1-(4-Bromophenyl)ethylamine, (R)-4-Chloro-α-methylbenzylamine, (S)-4-Chloro-α-methylbenzylamine, Cinchonidine, (+)-Cinchonine, (R)-(+)-N,α-Dimethylbenzylamine, (S)-(−)-N,α-Dimethylbenzylamine, (R)-(+)-N,N-Dimethyl-1-phenylethylamine, (S)-(−)-N,N-Dimethyl-1-phenylethylamine, (R)-5,5-Dimethyl-6-phenyl-3,4,5,6-tetrahydropyrimidine. (S)-5,5-Dimethyl-6-phenyl-3,4,5,6-tetrahydropyrimidine. (R)-(−)-3,5-Dinitro-N-(1-phenylethyl)benzamide, (S)-(+)-3,5-Dinitro-N-(1-phenylethyl)benzamide, (1R,2S)-(−)-Ephedrine, D-Glutamic acid, L-Glutamic acid, (R)-(+)-α-Methylbenzylamine, (S)-(−)-α-Methylbenzylamine, (R)-α-Methyl-4-nitrobenzylaminehydrochloride, (S)-α-Methyl-4-nitrobenzylaminehydrochloride, (R)-(+)-α-Methyl-4-pyridinemethanol, (S)-(−)-α-Methyl-4-pyridinemethanol, (S)-(−)-1-(2-Naphthyl)ethylamine, (S)-(−)-N-[1-(1-Naphthyl)ethyl]succinamic acid. (R)-(+)-N-(1-Phenylethyl) phthalamic acid, (S)-(−)-N-(1-Phenylethyl) phthalamic acid, (R)-(+)-N-(1-Phenylethyl) succinamic acid, (S)-(−)-N-(1-Phenylethyl) succinamic acid, Quinine, D-Valine, and L-Valine.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

2. Processes

The processes described herein provide functionalized payloads which have improved aqueous solubility compared with payloads linked to an unsubstituted cyclooctene. The functionalized payloads can be used as reagents in bioorthogonal conjugation or click reactions, and have use in various applications in the fields of chemistry, chemical biology, molecular diagnostics, and medicine, where they can be used to facilitate the selective manipulation of molecules, cells, particles and surfaces, and the tagging and tracking of biomolecules in vitro and in vivo. The processes described herein are performed using suitable reactions conditions and optionally one or more protecting groups as needed.

The term "reaction conditions" is intended to refer to the physical and/or environmental conditions under which a chemical reaction proceeds. Examples of reaction conditions include, but are not limited to, one or more of following: reaction temperature, solvent, pH, pressure, reaction time, mole ratio of reactants, the presence of a base or acid, one or more protecting groups, or catalyst, radiation, etc. Reaction conditions may be named after the particular chemical reaction in which the conditions are employed, such as, coupling conditions, hydrogenation conditions, acylation conditions, reduction conditions, etc. Reaction conditions for most reactions are generally known to those skilled in the art or can be readily obtained from the literature. Exemplary reaction conditions sufficient for performing the chemical transformations provided herein can be found throughout, and in particular, the examples below. It is also contemplated that the reaction conditions can include reagents in addition to those listed in the specific reaction.

The term "protecting group" refers to those groups intended to protect a given atom or functional group against undesirable reactions during synthetic procedures and includes, but is not limited to, silyl ethers, such as 2-(trimethylsilyl) ethoxymethyl (SEM) ether, or alkoxymethyl ethers, such as methoxymethyl (MOM) ether, tert-butoxymethyl (BUM) ether, benzyloxymethyl (BOM) ether or methoxyethoxymethyl (MEM) ether. Additional protecting groups include, tert-butyl, acetyl, benzyl, benzyloxycarbonyl (carbobenzyloxy, CBZ), p-methoxy benzyloxycarbonyl, p-nitrobenzyloxycarbonyl, tert-butoxycarbonyl (BOC), trifluoroacetyl, and the like. Certain protecting groups may be preferred over others due to their convenience or relative ease of removal, or due to their stereospecific effects in subsequent steps of the process. Additional suitable amino protecting groups are taught in T. W. Greene and P. G. M. Wuts, *Protecting Groups in Organic Synthesis*, Fifth Edition, Wiley, New York, 2014, and references cited therein which are all incorporated by reference in its entirety.

In one embodiment, the present disclosure provides a process for preparing a compound of formula I, or a salt thereof:

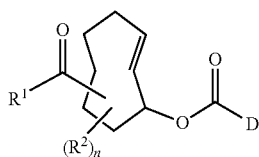

wherein
$R^1$ is selected from the group consisting of —$OR^4$, optionally substituted heterocyclyl, and an amino acid moiety;
n is 0, 1, 2, 3 or 4;
each $R^2$ is independently $C_{1-4}$alkyl, $C_{1-4}$haloalkyl, and $C_{1-4}$alkoxy;
D is a payload moiety; and
$R^4$ is hydrogen or $C_{1-4}$alkyl;
comprising contacting a compound of formula II:

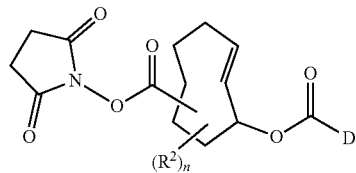

with HO—$R^4$, an optionally substituted heterocyclyl or an amino acid moiety, or a salt thereof, and a compound of formula III:

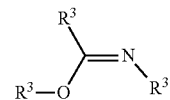

wherein each $R^3$ is independently $C_{1-4}$alkyl, in an organic solvent in the presence of a base.

In one embodiment, the present disclosure provides a process for preparing a compound of formula I, or a salt thereof:

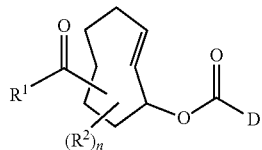

wherein
$R^1$ is an amino acid moiety;
n is 0, 1, 2, 3 or 4;
each $R^2$ is independently $C_{1-4}$alkyl, $C_{1-4}$haloalkyl, and $C_{1-4}$alkoxy; and
D is a payload moiety;
comprising contacting a compound of formula II:

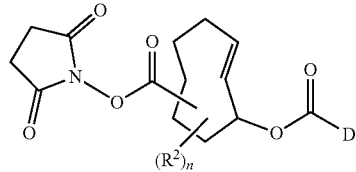

with an amino acid moiety, or a salt thereof, and a compound of formula III:

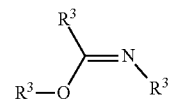

wherein each $R^3$ is independently $C_{1-4}$alkyl, in an organic solvent in the presence of a base.

In one embodiment, the present disclosure provides a process for preparing a compound of formula I, or a salt thereof:

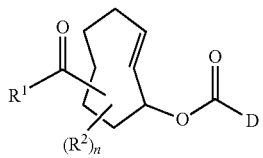

I wherein
R¹ is selected from the group consisting of G¹, OH, —NR$^{1c}$—C$_{1-4}$alkylene-G¹, —NR$^{1c}$—C$_{1-4}$alkylene-N(R$^{1d}$)$_2$, —N(R$^{1c}$)CHR$^{1e}$CO$_2$H, —N(R$^{1c}$)—C$_{1-6}$alkylene-CO$_2$H, —N(R¹)—C$_{2-4}$alkylene-(N(C$_{1-4}$alkylene-CO$_2$H)—C$_{2-4}$alkylene)$_m$-N(C$_{1-4}$alkylene-CO$_2$H)$_2$, —N(R$^{1c}$)CHR$^{1e}$C(O)OC$_{1-6}$alkyl, —N(R$^{1c}$)—C$_{1-6}$alkylene-C(O)OC$_{1-6}$alkyl, and —N(R$^{1f}$)—C$_{2-4}$alkylene-(N(C$_{1-4}$alkylene-C(O)OC$_{1-6}$alkyl)-C$_{2-4}$alkylene)$_m$-N(C$_{1-4}$alkylene-C(O)OC$_{1-6}$alkyl)$_2$;
R$^{1c}$ and R$^{1d}$, at each occurrence, are independently hydrogen or C$_{1-4}$alkyl;
R$^{1e}$ is —C$_{1-4}$alkylene-CO$_2$H, —C$_{1-4}$alkylene-CONH$_2$, or —C$_{1-4}$alkylene-OH;
R$^{1f}$ is hydrogen, C$_{1-6}$alkyl, or C$_{1-4}$alkylene-CO$_2$H;
G¹ is an optionally substituted heterocyclyl.
each R² is independently C$_{1-4}$alkyl, C$_{1-4}$haloalkyl, and C$_{1-4}$alkoxy;
D is a payload moiety;
n is 0, 1, 2, 3 or 4; and
m is 0, 1, 2, or 3;
comprising contacting a compound of formula II:

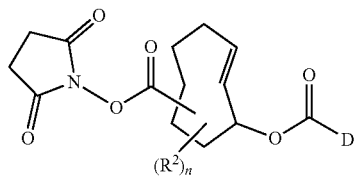

II with a suitable reagent and a compound of formula III:

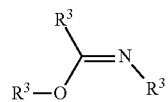

III wherein each R³ is independently C$_{1-4}$alkyl, in an organic solvent in the presence of a base.
In certain embodiments, R¹ is selected from the group consisting of G¹, OH, —NR$^{1c}$—C$_{1-4}$alkylene-G¹, —NR$^{1c}$—C$_{1-4}$alkylene-N(R$^{1d}$)$_2$, —N(R$^{1c}$)CHR$^{1e}$CO$_2$H, —N(R$^{1c}$)CH$_2$CO$_2$H, and —N(R$^{1f}$)—CH$_2$CH$_2$—(N(CH$_2$CO$_2$H)CH$_2$CH$_2$)$_m$-N(CH$_2$CO$_2$H)$_2$;
R$^{1e}$ is —C$_{1-4}$alkylene-CO$_2$H;
R$^{1f}$ is hydrogen or —C$_{1-4}$alkylene-CO$_2$H;
G¹ is a 4- to 8-membered monocyclic heterocyclyl containing a first nitrogen and optionally one additional heteroatom selected from nitrogen, oxygen, and sulfur, G¹ being attached at the first nitrogen and optionally substituted with 1-4 substituents independently selected from the group consisting of C$_{1-4}$alkyl, C$_{1-4}$haloalkyl, halo, cyano, OH, —OC$_{1-4}$alkyl, and oxo; and
m is 0, 1, or 2.

In certain embodiments, R¹ is an amino acid moiety.

In certain embodiments, the compound of formula III is N,O-bis(trimethylsilyl) acetamide.

In certain embodiments, the organic solvent comprises DMF, DCM or a mixture thereof.

In certain embodiments, the base comprises an organic base. In certain embodiments, the base comprises an amine base. In certain embodiments, the base comprises DIPEA.

In certain embodiments, the contacting comprises stirring at room temperature for about 24 hours.

In certain embodiments, the process further comprises preparing the compound of formula II by reacting a compound of formula IV:

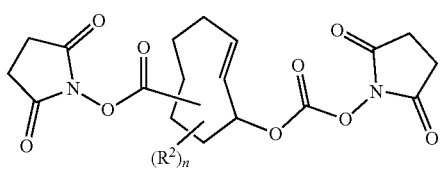

IV with a payload moiety, or a salt thereof, in an organic solvent in the presence of a base.

In certain embodiments, the organic solvent comprises DMF, DCM or a mixture thereof.

In certain embodiments, the base comprises an organic base. In certain embodiments, the base comprises an amine base. In certain embodiments, the base comprises DIPEA.

In certain embodiments, the contacting comprises stirring at room temperature for about 1 to 2 hours.

In certain embodiments, the compound of formula I is represented by formula IA:

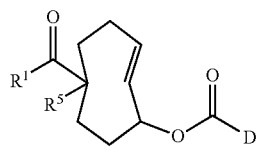

IA wherein
R¹ is selected from the group consisting of —OR⁴, optionally substituted heterocyclyl, and an amino acid moiety;
R⁴ is hydrogen or C$_{1-4}$alkyl;
R⁵ is hydrogen or C$_{1-4}$alkyl; and
D is a payload moiety;

and the compound of formula II is represented by formula IIA:

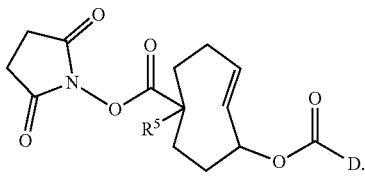

IIA

In certain embodiments, the compound of formula I is represented by formula IA:

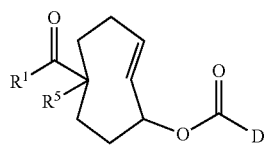

IA wherein
R[1] is an amino acid moiety;
R[5] is hydrogen or $C_{1-4}$alkyl; and
D is a payload moiety;
and the compound of formula II is represented by formula IIA:

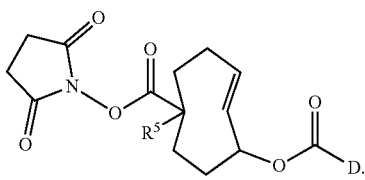

IIA

In certain embodiments, the compound of formula IV is represented by formula IVA:

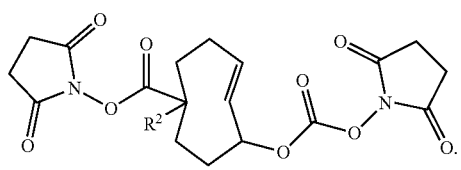

IVA

Also provided herein is a process of preparing a compound of formula X, or a salt thereof:

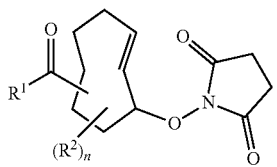

X wherein
R[1] is selected from the group consisting of —OR[4], optionally substituted heterocyclyl, and an amino acid moiety;
n is 0, 1, 2, 3 or 4;
each R[2] is independently $C_{1-4}$alkyl, $C_{1-4}$haloalkyl, and $C_{1-4}$alkoxy; and
R[4] is hydrogen or $C_{1-4}$alkyl;
comprising contacting a compound of formula IV:

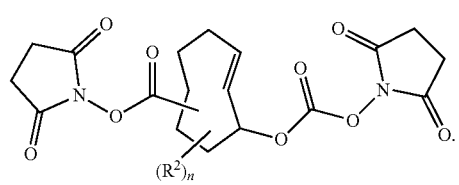

IV with HO—R[4], an optionally substituted heterocyclyl or an amino acid moiety, or a salt thereof, and a compound of formula III:

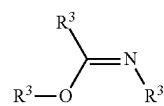

III wherein each R[3] is independently $C_{1-4}$alkyl, in an organic solvent in the presence of a base.

Also provided herein is a process of preparing a compound of formula X, or a salt thereof:

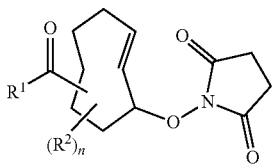

X wherein
R[1] is an amino acid moiety;
n is 0, 1, 2, 3 or 4;
each R[2] is independently $C_{1-4}$alkyl, $C_{1-4}$haloalkyl, and $C_{1-4}$alkoxy; and
comprising contacting a compound of formula IV:

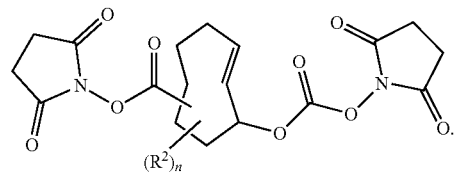

IV with an amino acid, or a salt thereof, and a compound of formula III:

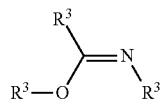

wherein each $R^3$ is independently $C_{1-4}$alkyl, in an organic solvent in the presence of a base.

In certain embodiments, the compound of formula III is N,O-bis(trimethylsilyl) acetamide.

In certain embodiments, the organic solvent comprises DMF, DCM or a mixture thereof.

In certain embodiments, the base comprises an organic base. In certain embodiments, the base comprises an amine base. In certain embodiments, the base comprises DIPEA.

In certain embodiments, the contacting comprises stirring at room temperature for about 24 hours.

In certain embodiments, the compound of formula X is represented by formula XA:

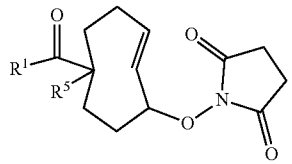

and the compound of formula IV is represented by formula IVA:

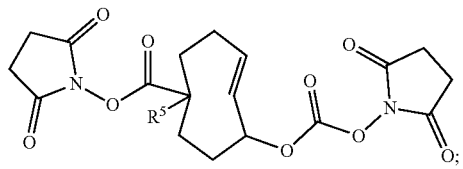

wherein $R^1$ is as defined herein, and $R^5$ is hydrogen or $C_{1-4}$alkyl.

In certain embodiments, provided is a process for preparing the compound of formula IV wherein $R^2$ and n are as defined herein, or a salt thereof, comprising contacting a compound of formula V, or a salt thereof:

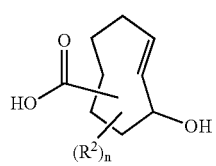

with N,N'-disuccinimidylcarbonate in an organic solvent in the presence of a base.

In certain embodiments, the organic solvent comprises acetonitrile. In certain embodiments, the organic solvent comprises dry acetonitrile.

In certain embodiments, the base comprises an organic base. In certain embodiments, the base comprises an amine base. In certain embodiments, the base comprises DIPEA.

In certain embodiments, the contacting comprises stirring at room temperature.

In certain embodiments, the compound of formula V is represented by formula VA:

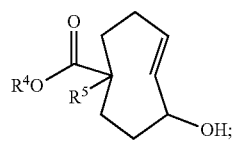

wherein $R^4$ is hydrogen or $C_{1-4}$alkyl and $R^5$ is hydrogen or $C_{1-4}$alkyl.

Also provided is a process of preparing a compound of formula I, or a salt thereof:

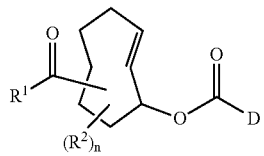

wherein
$R^1$ is selected from the group consisting of $-OR^4$, optionally substituted heterocyclyl, and an amino acid moiety;
n is 0, 1, 2, 3 or 4;
each $R^2$ is independently $C_{1-4}$alkyl, $C_{1-4}$haloalkyl, and $C_{1-4}$alkoxy;
D is a payload moiety; and
$R^4$ is hydrogen or $C_{1-4}$alkyl;
comprising contacting a compound of formula X, or a salt thereof:

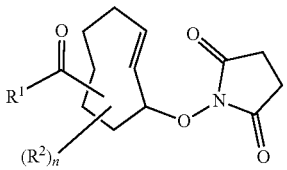

with a payload moiety, or a salt thereof, in an organic solvent in the presence of a base.

Also provided is a process of preparing a compound of formula I, or a salt thereof:

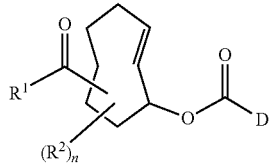

wherein
R¹ is an amino acid moiety;
n is 0, 1, 2, 3 or 4;
each R² is independently $C_{1-4}$alkyl, $C_{1-4}$haloalkyl, and $C_{1-4}$alkoxy; and
D is a payload moiety;
comprising contacting a compound of formula X, or a salt thereof:

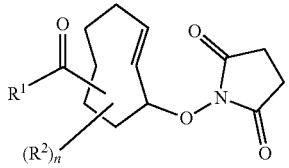

with a payload moiety, or a salt thereof, in an organic solvent in the presence of a base.

In certain embodiments, the organic solvent comprises DMF, DCM or a mixture thereof.

In certain embodiments, the base comprises an organic base. In certain embodiments, the base comprises an amine base. In certain embodiments, the base comprises DIPEA.

In certain embodiments, the contacting comprises stirring at room temperature for about 1 to 2 hours.

In certain embodiments, the compound of formula I is represented by formula IA:

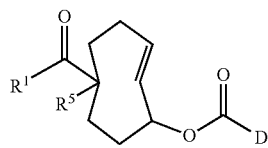

and the compound of formula X is represented by formula XA:

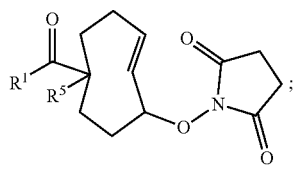

wherein R⁵ is hydrogen or $C_{1-4}$alkyl.

Also provided herein is a process of preparing a composition comprising a compound of formula IV, or a salt thereof:

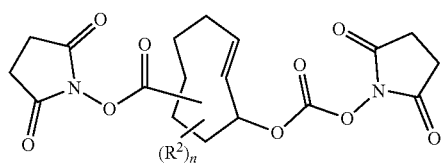

wherein
n is 0, 1, 2, 3, or 4; and
each R² independently hydrogen or $C_{1-4}$alkyl;
comprising contacting one equivalent of a compound of formula V, or a salt thereof:

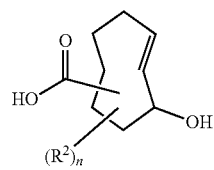

with 3-5 equivalents of N,N'-disuccinimidylcarbonate in 15-25 volumes of an anhydrous organic solvent in the presence of a base at a temperature from 15-30° C. for 5-10 hours.

In certain embodiments, the process further comprises adding the composition comprising a compound of formula IV to 40-60 volumes of water at room temperature to form an aqueous product mixture.

In certain embodiments, the process further comprises isolating a solid formed in the aqueous product mixture.

In certain embodiments, the process further comprises triturating the solid in acetonitrile at a temperature of from about 30 to about 50° C. to form a triturated solid.

In certain embodiments, the process further comprises isolating the triturated solid.

In certain embodiments, the anhydrous organic solvent is anhydrous acetonitrile.

In certain embodiments, the base is a trialkylamine base.

In certain embodiments, the base is diisopropylethylamine.

In certain embodiments, the compound of formula IV is represented by formula IVA:

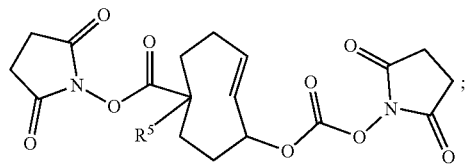

and the compound of formula V is represented by formula VA:

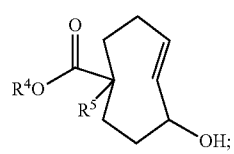

wherein R⁴ is hydrogen or $C_{1-4}$alkyl and R⁵ is hydrogen or $C_{1-4}$alkyl.

Also provided herein is a process for resolving a composition comprising one or more stereoisomers of a compound of formula VI, or a salt thereof:

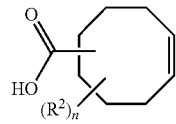

VI wherein
n is 0, 1, 2, 3, or 4;
each $R^2$ is independently $C_{1-4}$alkyl, $C_{1-4}$haloalkyl, and $C_{1-4}$alkoxy;
comprising the steps of:
(a) contacting a composition comprising one or more stereoisomers of formula VI with a chiral base to provide a chiral salt of the compound of formula VI;
(b) cooling the composition of step (a);
(c) isolating the chiral salt of the compound of formula VI; and
(d) hydrolyzing the chiral salt of the compound of formula VI to provide the enantiomerically enriched composition comprising a compound of formula VI, or a salt thereof.

In certain embodiments, the chiral base is cinchonidine.

In certain embodiments, the contacting of step (a) is performed in a solvent selected from acetone/water or acetone/isopropyl alcohol.

In certain embodiments, the cooling of step (b) is performed at a temperature at or below about 15° C.

In certain embodiments, the cooling of step (b) is at a temperature of from about 10 to about 15° C.

In certain embodiments, the cooling of step (b) is maintained for at least about 8 hours.

In certain embodiments, the isolating of step (c) is via filtration.

In certain embodiments, the process further comprises dissolving the chiral salt of the compound of formula VI obtained from step (c) in a suitable solvent, and repeating steps (b) and (c) prior to step (d).

In certain embodiments, the process further comprises the steps of dissolving the chiral salt of the compound of formula VI obtained from step (c) in a suitable solvent, and repeating steps (b) and (c) two, three, four, five or six times prior to step (d).

In certain embodiments, the compound of formula VI is represented by formula VIA:

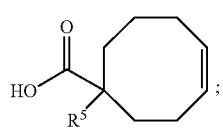

VIA wherein $R^5$ is hydrogen or $C_{1-4}$alkyl.

Also provided herein is a process for the preparation of an enantiomerically enriched composition comprising a compound of formula VII, or a salt thereof:

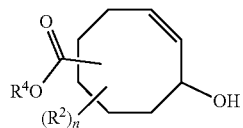

VII wherein
n is 0, 1, 2, 3 or 4;
each $R^2$ is independently $C_{1-4}$alkyl, $C_{1-4}$haloalkyl, and $C_{1-4}$alkoxy; and
$R^4$ is independently hydrogen or $C_{1-4}$alkyl;
comprising sequentially contacting an enantiomerically enriched composition of a compound of formula VI, or a salt thereof:

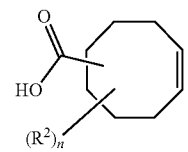

VI with: (i) a solution comprising KI and $I_2$, (ii) a base, and (iii) a hydrolyzing composition comprising a base and a compound of formula $R^4$—OH, to provide the enantiomerically enriched composition of a compound of formula VII, or a salt thereof.

Also provided herein is a process wherein the compound of formula VII is represented by formula VIIA:

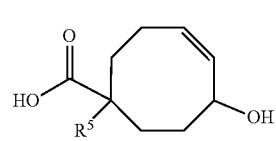

VIIA and the compound of formula VI is represented by formula VIA:

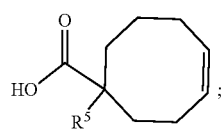

VIA wherein $R^5$ is hydrogen or $C_{1-4}$alkyl.

Also provided herein is a process for the preparation of an enantiomerically enriched composition comprising a compound of formula VIIB, or a salt thereof:

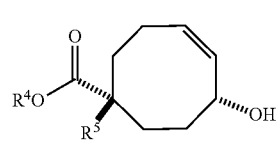

VIIB wherein R⁴ is hydrogen or C₁₋₄alkyl R⁵ is hydrogen or C₁₋₄alkyl, comprising hydrolyzing an enantiomerically enriched composition of a compound of formula IXB, or a salt thereof:

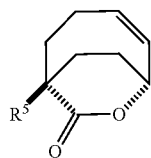

IXB with a hydrolyzing composition comprising a base and a compound of formula R⁴—OH, to provide the enantiomerically enriched composition of a compound of formula VIIB, or a salt thereof.

Also provided herein is a process for resolving a composition comprising one or more stereoisomers of a compound of formula VIIA, or a salt thereof:

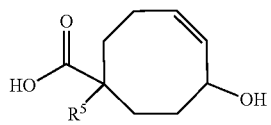

VIIA wherein

R⁵ is hydrogen or C₁₋₄alkyl, comprising the steps of:
(a) contacting a composition comprising one or more stereoisomers of formula VIIA with a chiral base to provide a chiral salt of the compound of formula VIIA;
(b) cooling the composition of step (a);
(c) isolating the chiral salt of the compound of formula VIIA; and
(d) hydrolyzing the chiral salt of the compound of formula VIIA to provide the enantiomerically enriched composition comprising a compound of formula VIIA, or a salt thereof.

In certain embodiments, the chiral base is (R)-1-amino-2-propanol. In certain embodiments, the chiral base is L-phenylalaninol. In certain embodiments, the chiral base is (S)-phenylglycinol. In certain embodiments, the chiral base is (S)-diphenyl-2-pyrrolidine methanol.

Also provided herein is a process for the preparation of an enantiomerically enriched composition comprising a compound of formula IXB, or a salt thereof:

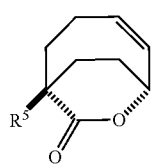

IXB wherein R⁵ is hydrogen or C₁₋₄alkyl, comprising contacting an enantiomerically enriched composition of a compound of formula VIIIB, or a salt thereof:

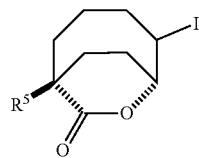

VIIIB with a base to provide the enantiomerically enriched composition of a compound of formula IXB, or a salt thereof.

Also provided herein is a process for the preparation of an enantiomerically enriched composition comprising a compound of formula VIIIB, or a salt thereof:

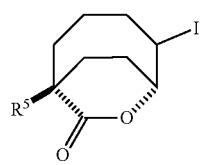

VIIIB wherein R⁵ is hydrogen or C₁₋₄alkyl, comprising contacting an enantiomerically enriched composition of a compound of formula VIB, or a salt thereof:

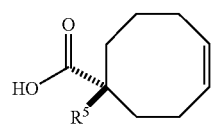

VIB with a solution comprising KI and I₂ to provide the enantiomerically enriched composition of a compound of formula VIIIB, or a salt thereof.

Also provided herein is a process for the preparation of an enantiomerically enriched composition comprising a compound of formula VIIB, or a salt thereof:

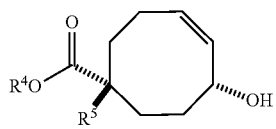

VIIB wherein
R⁴ is hydrogen or C₁₋₄alkyl; and
R⁵ is hydrogen or C₁₋₄alkyl;
comprising the steps of:
(a) contacting an enantiomerically enriched composition of a compound of formula VIB, or a salt thereof:

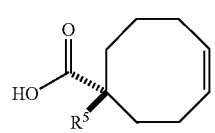

VIB with a solution comprising KI and I₂ to provide an enantiomerically enriched composition of a compound of formula VIIIB, or a salt thereof:

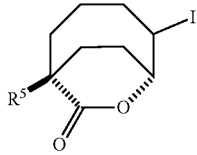

VIIIB (b) contacting the enantiomerically enriched composition of a compound of formula VIIIB with a base to provide an enantiomerically enriched composition of a compound of formula IXB, or a salt thereof:

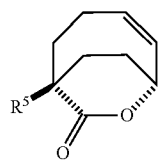

IXB (c) hydrolyzing the enantiomerically enriched composition of a compound of formula IXB, or a salt thereof, with a hydrolyzing composition comprising a base and a compound of formula $R^4$—OH, to provide the enantiomerically enriched composition of a compound of formula VIIB, or a salt thereof.

Also provided herein is a process for the preparation of an enantiomerically enriched composition comprising a compound of formula VB, or a salt thereof:

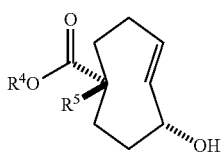

VB wherein
$R^4$ is hydrogen or $C_{1-4}$alkyl; and
$R^5$ is hydrogen or $C_{1-4}$alkyl;
comprising isomerizing an enantiomerically enriched composition of a compound of formula VIIB, or a salt thereof:

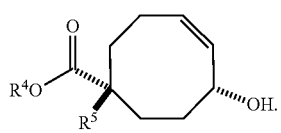

VIIB

In certain embodiments, the isomerizing comprises exposing the compound of formula VA to UV light.

In certain embodiments, when $R^4$ is $C_{1-4}$alkyl, the process further comprises a hydrolyzing step to convert $R^4$ to hydrogen.

Also provided herein is a process for the preparation of an enantiomerically enriched composition comprising a compound of formula IVB, or a salt thereof:

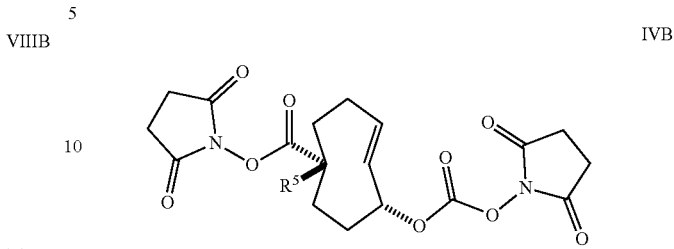

IVB wherein $R^5$ is hydrogen or $C_{1-4}$alkyl, comprising contacting an enantiomerically enriched composition of a compound of formula VB, or a salt thereof:

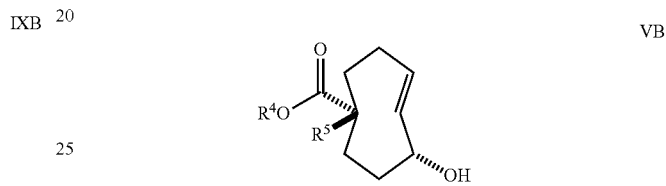

VB with N,N'-disuccinimidyl carbonate (DSC) under conditions to provide the enantiomerically enriched composition comprising a compound of formula IVB.

In certain embodiments of any of the formulas described herein, $R^1$ is a glycine moiety. In certain embodiments of any of the formulas described herein, $R^1$ is glycine.

In certain embodiments of any of the formulas described herein, n is 1.

In certain embodiments of any of the formulas described herein, $R^2$ is $C_{1-4}$ alkyl. In certain embodiments of any of the formulas described herein, $R^2$ is methyl.

In certain embodiments of any of the formulas described herein, $R^5$ is methyl.

Amino Acid Moieties

The term "amino acid" refers to both natural and unnatural amino acids. In certain embodiments, the amino acid moiety is a natural amino acid. The natural amino acids comprise the twenty proteinogenic amino acids encoded directly by triplet codons in the genetic code, and include alanine (ala, A), arginine (arg, R), asparagine (asn, N) aspartic acid (asp, D), cysteine (cys, C) glutamine (gln, Q) glutamic acid (glu, E) glycine (gly, G) histidine (his, H) isoleucine (ile, I) leucine (leu, L) lysine (lys, K) methionine (met, M) phenylalanine (phe, F) proline (pro, P) serine (ser, S) threonine (thr, T) tryptophan (trp, W) tyrosine (tyr, Y) and valine (val, V).

The amino acid moiety may also comprise an unnatural amino acid. In its broadest meaning, the term "amino acid moiety" comprises any organic compound with an amine (—NH₂) and a carboxylic acid (—CO₂H) functional group.

In certain embodiments, the amino acid moiety is selected from the group consisting of —$NR^{1c}$—$C_{1-4}$alkylene-optionally substituted heterocyclyl, —$NR^{1c}$—$C_{1-4}$alkylene-N($R^{1d}$)₂, —N($R^{1c}$)CHR$^{1e}$CO₂H, —N($R^{1c}$)—$C_{1-6}$alkylene-CO₂H, —N($R^{1f}$)—$C_{2-4}$alkylene-(N($C_{1-4}$alkylene-CO₂H)—$C_{2-4}$alkylene)$_m$-N($C_{1-4}$alkylene-CO₂H)₂, —N($R^{1c}$)CHR$^{1c}$(O)OC$_{1-6}$alkyl, —N($R^{1c}$)—$C_{1-6}$alkylene-C(O)OC$_{1-6}$alkyl, and —N($R^{1f}$)—$C_{2-4}$alkylene-(N($C_{1-4}$alkylene-C(O)OC$_{1-6}$alkyl)-$C_{2-4}$alkylene)$_m$-N($C_{1-4}$alkylene-C(O)OC$_{1-6}$alkyl)₂; wherein $R^{1c}$ and $R^{1d}$ are each independently hydrogen or $C_{1-4}$alkyl;

$R^{1e}$ is —$C_{1-4}$alkylene-$CO_2H$, —$C_{1-4}$alkylene-$CONH_2$, or —$C_{1-4}$alkylene-OH;

$R^{1f}$ is hydrogen, —$C_{1-6}$alkyl, or —$C_{1-4}$alkylene-$CO_2H$; and m is 0, 1, 2, or 3.

In certain embodiments, the amino acid moiety is glycine. In certain embodiments, the amino acid moiety is alanine.

Payloads

As used herein, a "payload moiety" refers to a payload D minus its nucleophilic group such as NH, $NC_{1-4}$alkyl, O, or S that attaches to a linker or minus its electrophilic group such as C(O) that attaches to a linker, i.e., the remainder of the payload. The term "payload", in general, refers to an agent for delivery to a target site in a subject, and includes, but isn't limited to, therapeutic agents, diagnostic agents, targeting agents, and the like.

In some embodiments, the payload is a therapeutic agent, such as an antibiotic agent, antifungal agent, antiviral agent, anticancer agent, cardiovascular agent, CNS agent, anti-inflammatory/anti-arthritic agent, anti-TB/anti-leprosy agent, anti-histaminic/respiratory disorder agent, a corticosteroid agent, immunosuppressant agent, or anti-ulcer agent. Particular therapeutic agents include paclitaxel, doxorubicin, daunorubicin, etoposide, irinotecan, SN-38, docetaxel, gemcitabine, podophyllotoxin, carmustine, ixabepilone, patupilone, cyclosporin A, rapamycin, amphotericin, vancomycin, daptomycin, doxycycline, ceftriaxone, trimethoprim, sulfamethoxazole, acyclovir, nystatin, amphotericin B, flucytosine, emtricitabine, gentamicin, colistin, L-dopa, oseltamivir, cefalexin, 5-aminolevulinic acid, cysteine, celecoxib, and nimodipine.

In certain embodiments, the payload moiety is an anthracycline moiety, an auristatin moiety, a glycopeptide antibiotic moiety, or a lipopeptide antibiotic moiety.

In certain embodiments, the payload moiety is a doxorubicin moiety, daunorubicin moiety, monomethyl auristatin E moiety, vancomycin moiety or daptomycin moiety.

In certain embodiments, D is an antibiotic agent, antifungal agent, antiviral agent, anticancer agent, cardiovascular agent, CNS agent, anti-inflammatory/anti-arthritic agent, anti-TB/anti-leprosy agent, anti-histaminic/respiratory disorder agent, a corticosteroid agent, immunosuppressant agent, or anti-ulcer agent.

In certain embodiments, D is an antibiotic. Suitable antibiotics include, but are not limited to β-lactams, including penicillins and cephalosporins, such as thienamycins, monobactams, β-lactamade inhibitors and methoxypeniciuins: aminoglycosides, including streptomycin, gentamicin, kanamycin, tobramycin, amikacin, neomycin, ribostamycin, micronomicin and astromicin: tetracyclines, including tetracycline, oxytetracycline, chlortetracycline and doxycycline: chloramphenicols, including chloramphenicol and thiamphenicol: macrolides, including erythromycin, albomycin, erythromycin estolate, erythromycin ethylsuccinate, azithromycin, acetylspiramycin, midecamycin and josamycin; other antibiotics acting on Gram-positive bacteria, such as lincomycin, clindamycin, vancomycin and bacitracin: other antibiotics acting on Gram bacteria, such as polymyxin, fosfomycin, ciramycin, cycloserine and rifampicin: antifungal antibiotics, such as griseofulvin: anticancer antibiotics, such as mitomycin, actinomycin D, bleomycin and Adriamycin; and immunosuppressive antibiotics, such as cyclosporine.

In certain embodiments, D is an anticancer drug, an anticoagulant, a microbial immunosuppressive drug, or an anti-restenosis drug. The anticancer drug may be one or more selected from methotrexate, purines, pyrimidines, plant alkaloids, cpothilones, triptolide compounds, antibiotics (notably actinomycin D), hormones and antibodies. From among the plant alkaloids, mention may notably be made of paclitaxel, doxorubicin, maytansin, auristatin, calicheamycin, duocarmycin, tubulysin and camptothecin. The anticoagulant may be one or more selected from heparin, aspirin, hirudin, colchicine and platelet GPIIb/IIIa receptor antagonists.

The platelet GPIIb/IIIa receptor antagonists may be one or more selected from tirofiban, abciximab and eptifibatide. The microbial immunosuppressive drug may be one or more selected from cyclosporin A, tacrolimus and its analogues, despergualin, mycophenolate esters, rapamycin and its derivatives, FR-900520 substance from *Streptomyces* strains, FR-900523 substance from *Streptomyces* strains, daclizumab, pentanamide, kanglemycin C, spergualin, prodigiosin-25C, tranilast, myriocin, cyclosporin C, bredinin, mycophenolic acid, brefeldin A and ketosteroids. The anti-restenosis drug may be one or more selected from batimastat, metalloproteinase inhibitors, 17β-estradiol, NO donors, 2-chlorodeoxyadeno sine, 2-deoxycoformycin, fingolimod, mycophenolate sodium, ISATX247 (a cyclosporin A derivative), elsibucol, daclizumab, basiliximab, anti-thymocyte globulin, everolimus, methotrexate, neoral, cyclophosphamide, brequinar sodium, leflunomide and mizoribine.

In certain embodiments, D is an anticancer drug. Exemplary anti-cancer drugs include, but are not limited to, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimalcate, Afinitor (Everolimus), Aldara (Imiquimod), Aldesleukin, Alemtuzumab, Alimta (Pemetrexed Disodium), Aloxi (Palonosctron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bicalutamide, Bleomycin, Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, Carboplatin-Taxol, Carfilzomib, Casodex (Bicalutamide), CecNU (Lomustine), Cerubidine (Daunorubicin Hydrochloride), Cervarix (Recombinant HPV Bivalent Vaccine), Cetuximab, Chlorambucil, Chlorambucil-Prednisone, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), Folfiri, Folfiri-Bevacizumab, Folfiri-Cetuximab, Folfirinox, Folfox (Leucovorin, Fluorouracil, Oxaliplatin), Folotyn (Pralatrexate), FU-LV, Fulvestrant, Gardasil (Recombinant HPV Quadrivalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Herceptin (Trastuzumab), HPV Bivalent Vaccine, Recombinant, HPV Quadrivalent Vaccine, Recombinant, Hycamtin (Topotecan Hydrochloride), Hyper-CVAD, Ibritumomab Tiuxetan, Ibrutinib, ICE, Iclusig (Ponatinib Hydrochloride), Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), OEPA, OPPA, Oxaliplatin, Paclitaxel, Paclitaxel Albumin-stabilized Nanoparticle Formulation, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Radium 223 Dichloride, Raloxifene Hydrochloride, Rasburicase, R-CHOP, R-CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), Stanford V, Sterile Talc Powder (Talc), Steritalc (Talc), Stivarga (Regorafenib), Sunitinib Malate, Sutent (Sunitinib Malate), Sylatron (Peginterferon Alfa-2b), Synovir (Thalidomide), Synribo (Omacetaxine Mepesuccinate), Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VelP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), Xelox, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), and Zytiga (Abiraterone Acetate).

In certain embodiments, D is a PBD dimer, calicheamicin, speromycin, tubulysin B, rhizoxin, dolastatin, didemnin B, camptothecin, CBI, temsirolimus, actinomycin D, epothilone B, taxol, cryptophycin, SN38, velcade, bruceantin, DAVLBH, DM1, Phyllanthoside, Alimta, T2 Toxin, MMC, vantalanib, vinorelbine, brefeldin, sunitinib, daunomycin, semaxanib, tarceva, iressa, irinotecan, LY-541503, geldanomycin, gemcitabine, methotrexate, gleevec, topotecan, bleomycin, doxorubicin, cisplatin, N-mustards, etoposide, or 5-FU.

In certain embodiments, D is an anthracycline. In certain embodiments, D is a taxane. In certain embodiments, D is gemcitabine. In certain embodiments, D is doxorubicin. In certain embodiments, D is docetaxel. In certain embodiments, D is SN38. In certain embodiments, D is monomethyl auristatin E. In certain embodiments, D is dexamethasone. In certain embodiments, D is celecoxib. In certain embodiments, D is gentamicin.

In certain embodiments, D is an intracellular permeation enhancing agent. For example, D may be a functionalized ketoacid, 6-oxo-6-phenylhexanoic acid, 8-oxo-8-phenyloctanoic acid, 8-(2,5-dichlorophenyl)-8-oxooctanoic acid, a functionalized ketoester or aldehyde, a modified amino acid, modified amino acids, N-[8-(2-hydroxybenzoyl)aminooctanoic acid, N-[8-(2-hydroxybenzoyl)aminodecanoic acid, N-(5-chlorosalicyloyl)-8-aminocaprylic acid, N-[4-(4-chloro-2-hydroxybenzoyl)aminol butanoic acid, 2-ethylhexyl 2-hydroxybenzoate, 5-cyclohexyl-5-oxovaleric acid, 6-cyclohexyl-6-oxohexanoic acid, 7-cyclohexyl-7-oxoheptanoic acid, 8-cyclohexyl-8-oxooctanoic acid, 4-cyclopentyl-4-oxobutyric acid, 5-cyclopentyl-5-oxovaleric acid, 6-cyclopentyl-6-oxohexanoic acid, 7-cyclopentyl-7-oxoheptanoic acid, 8-cyclopentyl-8-oxooctanoic acid, 4-cyclobutyl-4-oxobutyric acid, 5-cyclobutyl-5-oxovaleric acid, 6-cyclobutyl-6-oxohexanoic acid, 7-cyclobutyl-7-oxoheptanoic acid, 8-cyclobutyl-8-oxooctanoic acid, 4-cyclopropyl-4-oxobutyric acid, 5-cyclopropyl-5-oxovaleric acid, 6-cyclopropyl-6-oxohexanoic acid, 7-cyclopropyl-7-oxoheptanoic acid, 8-cyclopropyl-8-oxooctanoic acid, 8-[(3-methylcyclohexyl)oxy]octanoic acid, 7-[(3-methylcyclohexyl)oxy]heptanoic acid, 6-[(3-methylcyclohexyl)oxy]hexanoic acid, 5-[(3-methylcyclohexyl)oxy]pentanoic acid, 4-[(3-methylcyclohexyl)oxy]butanoic acid, 3-[(3-methylcyclohexyl)oxy]propanoic acid, octisalate, a diketopiperazines, saponin, an acylcarnitine, an alkanoylcholine, a taurodihydrofusidate, a sulphoxide, an oxazolidinone, a pyrrolidone, an alcohol or alkanol, a benzoic acid, a glycol, a surfactant, a terpene, a functionally effective salt of any of the foregoing, a derivative of any of the foregoing, or combinations thereof.

3. Compounds

In certain embodiments, the disclosure provides for intermediate compounds that are useful in the processes described herein. Thus, in one embodiment, provided is a compound selected from Table 1, or a salt thereof. In another embodiment, provided is an enantiomerically enriched composition comprising a compound selected from Table 1, or a salt thereof.

In Table 1, and as used throughout, it can be appreciated that the straight bolded or dashed bond is used to indicate relative stereochemistry, and the wedged bolded or dashed bond is used to indicate absolute stereochemistry. Where the composition is identified as enantiomerically enriched, it is intended that the composition comprises more than 50% of a single enantiomer, or at least about 55%, or at least about 60%, or at least about 65%, or at least about 70%, or at least about 75%, or at least about 80%, or at least about 85%, or at least about 90%, or at least about 95%, or at least about 97%, or about 99% ee.

TABLE 1

| Formula | Structure |
|---|---|
| IVC | |
| IVD | |
| VE-1 | 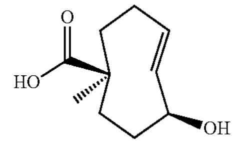 |
| VIC | 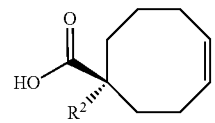 |
| VID | 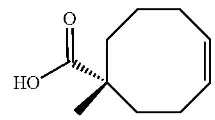 |
| VIE | 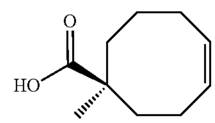 |
| VIIC | 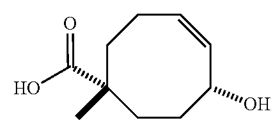 |
| VIID | 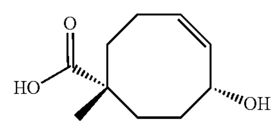 |
| VIIE | 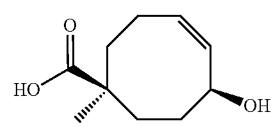 |
| VIIIC | 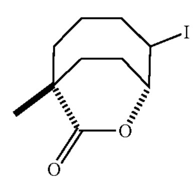 |
| VIIID | 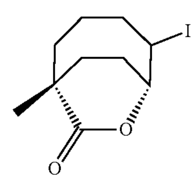 |
| VIIIE | 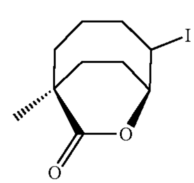 |

TABLE 1-continued

| Formula | Structure |
|---|---|
| IVE | 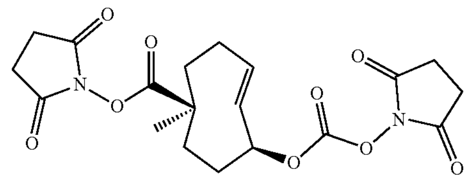 |
| VC-1 | 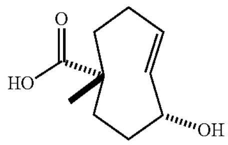 |
| VD-1 | 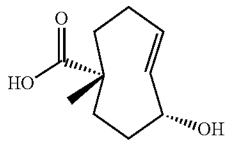 |
| IXC | 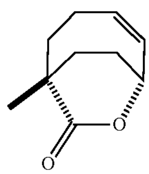 |
| IXD | 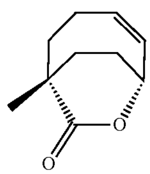 |
| IXE | 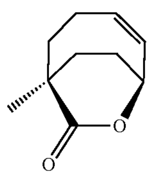 |
| XC | 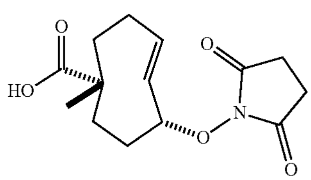 |
| XD | 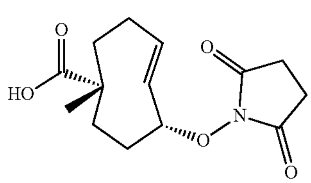 |
| XE | 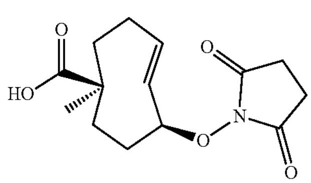 |

It is appreciated that certain features described herein, which are, for clarity, described in the context of separate embodiments, may also be provided in combination in a single embodiment. Conversely, various features described herein, which are, for brevity, described in the context of a single embodiment, may also be provided separately or in any suitable subcombination. All combinations of the embodiments pertaining to the chemical groups represented by the variables contained within Formula I, are specifically embraced by herein just as if each and every combination was individually and explicitly recited, to the extent that such combinations embrace compounds that result in stable compounds (i.e., compounds that can be isolated, characterized and tested for biological activity).

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Example 1: Chiral Resolution of (Z)-1-Methylcyclooct-4-ene-1-carboxylic acid

The following procedure produces a single enantiomer of compound IV in >97% ee on the kilogram-scale from racemic starting material, whereas previous reports form compound IV only on small scale as the racemate (Rossin, R. et al. *Bioconjugate Chem.* 2016, 1697-1706).

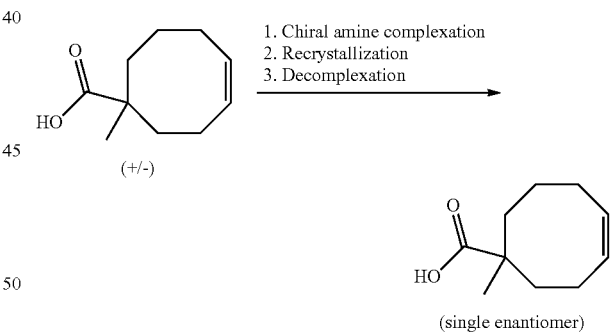

(Z)-1-methylcyclooct-4-ene-1-carboxylic acid (34.3 kg) was dissolved in EA (1355 kg). A solution of cinchonidine (60 kg) in DCM (460 kg) was charged at 35-40° C. The mixture was stirred for 4 h at 45° C., and then cooled down to 12° C. for another 8 hrs. The resulting suspension was filtered. The collected cake need to be further purified by recrystallization.

1$^{st}$ recrystallization: The salt (220 g) was dissolved completely in isopropanol (1 L) and acetone (5 L) at 60° C. The mixture was kept at 10-15° C. overnight. Filtered and dried to give 148 g product, 28.0% ee.

2$^{nd}$ recrystallization: The salt (148 g) was dissolved completely in Isopropanol (750 mL) and Acetone (3850 mL) at 60° C. The mixture was kept at 10-15° C. overnight. Filtered and dried to give 85.2 g product, 54.0% ee. The mother liquor was concentrated to give 62.8 g solid.

3$^{rd}$ recrystallization: The salt (85.2 g) was dissolved completely in Isopropanol (420 mL) and Acetone (2100 mL) at 60° C. The mixture was kept at 10-15° C. overnight. Filtered and dried to give 66.0 g product, 74.3% ee. The mother liquor was concentrated to give 19.0 g solid.

4$^{th}$ recrystallization: The salt (66.0 g) was dissolved completely in Isopropanol (330 mL) and Acetone (1650 mL) at 60° C. The mixture was kept at 10-15° C. overnight. Filtered and dried to give 42.7 g product, 83.4% ee. The mother liquor was concentrated to give 13.3 g solid.

5$^{th}$ recrystallization: The salt (42.7 g) was dissolved completely in Isopropanol (210 mL) and Acetone (1050 mL) at 60° C. The mixture was kept at 10-15° C. overnight. Filtered and dried to give 31.8 g product, 91.0% ee. The mother liquor was concentrated to give 10.9 g solid.

6$^{th}$ recrystallization: The salt (31.8 g) was dissolved completely in Isopropanol (160 mL) and Acetone (800 mL) at 60° C. The mixture was kept at 10-15° C. overnight. Filtered and dried to give 26.2 g product, 95.3% ee. The mother liquor was concentrated to give 5.6 g solid.

The concentrates of the mother liquors (ee >0%) can be combined and purified by several rounds of recrystallization to give more single isomer of 4.

The solid of the salt (single isomer of (Z)-1-methylcyclooct-4-ene-1-carboxylic acid with cinchonidine, 6 kg) was mixed with water (35.0 kg). The mixture was added HCl solution (2.0 kg of 12N conc. HCl diluted with 10.0 kg water) at 20-30° C. to adjust pH to 1. The resulting mixture was washed with Hexane (3×15.0 kg). The combined organic phases were washed with brine (10 kg). The organic phase was concentrated at 35-55° C. to give a single isomer of the title compound as an oil.

| Chromatography Conditions: | |
|---|---|
| Column | Superchiral S-AD |
| Column size | 0.46 cm I.D. × 15 cm L, 5 um |
| Injection | 5 μL |
| Mobile phase | Hexane/EtOH/DEA = 99/1/0.03 (v/v/v) |
| Flow rate | 1.0 mL/min |
| Wavelength | UV 210 nm and Advances Laser Polarimeter |
| Temperature | 15° C. |

% Ee Upgrade Following Salt Break:
- Salt of converted to free acid of (Z)-1-methylcyclooct-4-ene-1-carboxylic acid by addition of HCl
- Dissolve (Z)-1-methylcyclooct-4-ene-1-carboxylic acid and add desired enantiomer seed to induce crystallization
- Precipitation is observed, though analysis indicates there is no difference in % ee between the solid and supernatant
- Suggestive that racemate may exist as solid solution, making enrichment of acid form unfeasible Increasing Starting Material Purity:
- Racemate with low purity of 47% was spiked into pure enriched (Z)-1-methylcyclooct-4-ene-1-carboxylic acid (33% ee)
- Spiking of impurity did not impact the relative solubility of desired and undesired enantiomers
- Accordingly, no significant % ee improvement was observed using pure (Z)-1-methylcyclooct-4-ene-1-carboxylic acid compared to impure (Z)-1-methylcyclooct-4-ene-1-carboxylic acid for the resolution process Dependence of Relative Solubility of Desired/Undesired Enantiomers on % Ee:
- The solubility of desired and undesired enantiomers was measured in samples of various degrees of enantioenrichment, ranging from 0-88% ee
- For racemic material, solubility of the undesired enantiomer exceeds that of desired enantiomer
- However, once 46% ee is reached, the solubility trend reverses, with the solubility of the desired enantiomer salt exceeding that of the undesired enantiomer salt
- This switch complicates the development of a high yielding chiral resolution process to reach ≥97% ee starting from racemate The other solvents were screened and results shown below.

| | Starting solid | | Supernatant | | Final solid | | |
|---|---|---|---|---|---|---|---|
| Step | Weigh (g) | ee | Solvent | volume (mL) | ee | Yield | ee yield |
| salt formation | 0.83 | 0.0% | Acetone/H$_2$O (19:1) | 33.6 | 49.3% | 50.1% | 0.25 |
| 1$^{st}$ recrystallization | 0.506 | 53.70% | | 11.7 | 87.5% | 44.6% | 0.39 |
| 2$^{nd}$ recrystallization | 42.7 | 83.4% | IPA/Acetone 1:5 | 1260 | 91.0% | 74.5% | 0.68 |
| 3$^{rd}$ recrystallization | 31.8 | 91.0% | | 960 | 95.3% | 82.4% | 0.79 |

Final Purity: 81.2%
Overall Yield: 13.7%

Example 2: Large Scale Synthesis of Enantioenriched cis-(Z)-6-Hydroxy-1-methylcyclooct-4-ene-1-carboxylic acid Process for the production of single enantiomer (≥97% ee) cis-(Z)-6-hydroxy-1-methylcyclooct-4-ene-1-carboxylic acid on the kilogram-scale from racemic starting material. Literature reports synthesis of 17.5 g racemic cis-(Z)-6-hydroxy-1-methylcyclooct-4-ene-1-carboxylic acid. (Rossin, R. et al. *Bioconjugate Chem.* 2016, 1697-1706).

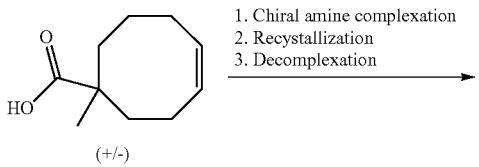

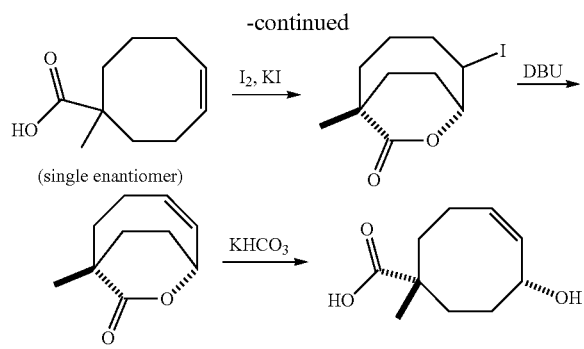

Compound 4 (34.3 kg) was dissolved in EA (1355 kg). A solution of cinchonidine (60 kg) in DCM (460 kg) was charged at 35-40° C. The mixture was stirred for 4 h at 45° C., and then cooled down to 12° C. for another 8 hrs. The resulting suspension was filtered. The collected cake need to be further purified by recrystallization.

$1^{st}$ recrystallization: The salt (220 g) was dissolved completely in isopropanol (1 L) and Acetone (5 L) at 60° C. The mixture was kept at 10-15° C. overnight. Filtered and dried to give 148 g product, 28.0% ee.

$2_{nd}$ recrystallization: The salt (148 g) was dissolved completely in isopropanol (750 ml) and Acetone (3850 mL) at 60° C. The mixture was kept at 10-15° C. overnight. Filtered and dried to give 85.2 g product, 54.0% ee. The mother liquor was concentrated to give 62.8 g solid.

$3^{rd}$ recrystallization: The salt (85.2 g) was dissolved completely in isopropanol (420 ml) and Acetone (2100 mL) at 60° C. The mixture was kept at 10-15° C. overnight. Filtered and dried to give 66.0 g product, 74.3% ee. The mother liquor was concentrated to give 19.0 g solid.

$4^{th}$ recrystallization: The salt (66.0 g) was dissolved completely in isopropanol (330 ml) and Acetone (1650 mL) at 60° C. The mixture was kept at 10-15° C. overnight. Filtered and dried to give 42.7 g product, 83.4% ee. The mother liquor was concentrated to give 13.3 g solid.

$5^{th}$ recrystallization: The salt (42.7 g) was dissolved completely in Isopropanol (210 mL) and Acetone (1050 mL) at 60° C. The mixture was kept at 10-15° C. overnight. Filtered and dried to give 31.8 g product, 91.0% ee. The mother liquor was concentrated to give 10.9 g solid.

$6^{th}$ recrystallization: The salt (31.8 g) was dissolved completely in Isopropanol (160 mL) and Acetone (800 mL) at 60° C. The mixture was kept at 10-15° C. overnight. Filtered and dried to give 26.2 g product, 95.3% ee. The mother liquor was concentrated to give 5.6 g solid.

The concentrates of the mother liquors (ee >0%) can be combined and purified by several rounds of recrystallization to give more single isomer of (Z)-1-methylcyclooct-4-ene-1-carboxylic acid.

The solid of the salt (single isomer of (Z)-1-methylcyclooct-4-ene-1-carboxylic acid with cinchonidine, 6 kg) was mixed with water (35.0 kg). The mixture was added HCl solution (2.0 kg of 12N conc. HCl diluted with 10.0 kg water) at 20-30° C. to adjust pH to 1. The resulting mixture was washed with Hexane (3×15.0 kg). The combined organic phases were washed with brine (10 kg). The organic phase was concentrated at 35-55° C. to give single isomer of (Z)-1-methylcyclooct-4-ene-1-carboxylic acid as an oil.

The product (2.8 kg) was taken in mixture of DCM (22.2 kg) and water (16.7 kg) and NaHCO$_3$ (4.8 kg) was added. The reaction mixture was cooled to 0-5° C. and added mixture of KI(8.2 kg) and iodine (8.4 kg) in portions. The reaction was stirred at room temperature for 2 h and then sampled for GC. When the starting material is no more than 2.0a % by GC, the reaction mixture was quenched slowly with sodium bisulfite (3.4 kg of sodium bisulfite in 16.7 kg of water) until clear solution appeared. Both the layers were separated and the aqueous layer was extracted with DCM (22.2 kg). The combined organic layer was washed with water (8.4 kg), dried with Na$_2$SO$_4$ (1.7 kg) and rotary evaporation yielded enantiomerically enriched 5-iodo-1-methyl-7-oxabicyclo[4.2.2]decan-8-one (quantitative) which was used in the next step without further purification.

The resulting product (4.8 kg) was dissolved in toluene (21.3 kg) and then DBU (2.9 kg) was added. The mixture was allowed to stand for 12 hrs at 25-30° C., after which it was heated under reflux for 4 hrs, at which point GC indicated full conversion (5-iodo-1-methyl-7-oxabicyclo [4.2.2]decan-8-one <3 a %). After cooling, the reaction mixture was washed with water (6.4 kg). The aqueous phases were extracted with toluene (10.7 kg). The organic phases was dried by Na$_2$SO$_4$ (2.9 kg) and then concentrated to a colorless oil (94% yield).

(Z)-1-methyl-7-oxabicyclo[4.2.2]dec-4-en-8-one (2.66 kg) was mixed with methanol (12.8 kg), KHCO$_3$ (16.0 kg) and water (0.03 kg). The mixture was hold at 28° C. for 24 hrs and monitored by HPLC. The reaction was deemed complete when the starting material NMT 26.0%. Filtered, and the cake was washed with methanol. The filtrate was concentrated at 35-55° C., and then EA (20 kg) and water (12.58 kg) was added. pH value of the mixture was adjusted to 2-3 by 2N HCl solution. Let the layers separated, and the aqueous phase was washed with EA (4×8.0 kg). The combined organic phases were washed with brine (17.2 kg), dried by Na$_2$SO$_4$ (1.3 kg) and then concentrated at 35-55° C. The residue was purified by chromatography using hexane and EA (50:1) as the eluent, affording the pure title product as a colorless oil. (Note: The starting material can be recycled and the mixed fractions also can be purified again to provide more products.)

Example 3: Synthesis of Enantioenriched 2,5-Dioxopyrrolidin-1-yl cis-(E)-6-((((2,5-dioxopyrrolidin-1-yl)oxy)carbonyl)oxy)-1-methylcyclooct-4-ene-1-carboxylate from cis-(E)-6-Hydroxy-1-methylcyclooct-4-ene-1-carboxylic acid Process for the robust synthesis of high purity 2,5-dioxopyrrolidin-1-yl cis-(E)-6-((((2,5-dioxopyrrolidin-1-yl)oxy)carbonyl)oxy)-1-methylcyclooct-4-ene-1-carboxylate from TCO starting material cis-(E)-6-Hydroxy-1-methylcyclooct-4-ene-1-carboxylic acid in 75% yield on the 100 gram-scale without the use of chromatography. Literature reference reports synthesis of 400 mg 2,5-dioxopyrrolidin-1-yl cis-(E)-6-((((2,5-dioxopyrrolidin-1-yl)oxy)carbonyl) oxy)-1-methylcyclooct-4-ene-1-carboxylate in 46% yield, requiring purification by silica gel chromatography (Rossin, R. et al. *Bioconjugate Chem.* 2016, 1697-1706).

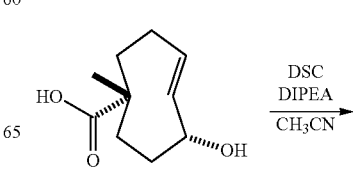

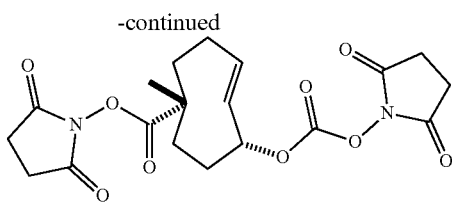

A mixture of cis-(E)-6-Hydroxy-1-methylcyclooct-4-ene-1-carboxylic acid (1 equiv.), N,N'-Disuccinimidyl carbonate (DSC) (4.3 equiv.), DIPEA (7.4 equiv.) in dry acetonitrile (20 volumes) is stirred at 22 to 25° C. until the intermediate 2,5-dioxopyrrolidin-1-yl cis-(E)-6-hydroxy-1-methylcyclooct-4-ene-1-carboxylate is less than 0.5% AUC by UPLC (7-9 h). The resulting suspension is added to DI water (50 volumes) at room temperature and the resulting mixture is stirred for about 15 min. The resulting solid suspension is filtered, washed with DI water (3×2 volumes), and dried on the filter under vacuum for approximately 1 h.

The solid crude 2,5-dioxopyrrolidin-1-yl cis-(E)-6-((((2,5-dioxopyrrolidin-1-yl)oxy)carbonyl)oxy)-1-methylcyclooct-4-ene-1-carboxylate is suspended in acetonitrile (~2 volumes) and mixed at 35 to 45° C. for approximately 1 h. The mixture is cooled to approximately 15° C. and filtered. The cake is washed with acetonitrile (2×1 volumes), and dried under vacuum on the filter for ~60 min to give enantiomerically enriched 2,5-dioxopyrrolidin-1-yl cis-(E)-6-((((2,5-dioxopyrrolidin-1-yl)oxy)carbonyl)oxy)-1-methylcyclooct-4-ene-1-carboxylate as a white to off white crystalline solid in ~99% AUC purity by UPLC at 214 nm in about 74-80% isolated yield.

From 61.8 g of cis-(E)-6-Hydroxy-1-methylcyclooct-4-ene-1-carboxylic acid, 106.0 g of 2,5-dioxopyrrolidin-1-yl cis-(E)-6-((((2,5-dioxopyrrolidin-1-yl)oxy)carbonyl)oxy)-1-methylcyclooct-4-ene-1-carboxylate was obtained in 98.6% AUC purity with 75.4% isolated yield.

| Analytical Method: | | | |
|---|---|---|---|
| Column | | | |
| Supelco Ascentis Express C18 (150 × 3.0 mm, 2.7 µm), Cat No. 53816-U | | | |
| Gradient Timetable | | | |
| Time (min) | A % (H$_2$O/0.1% TFA) | B % (ACN/0.1% TFA) | Flow (mL/min) |
| 0.00 | 98.00 | 2.00 | 0.600 |
| 12.00 | 5.00 | 95.00 | 0.600 |
| 14.00 | 5.00 | 95.00 | 0.600 |
| 14.10 | 98.00 | 2.00 | 0.600 |
| 16.00 | 98.00 | 2.00 | 0.600 |
| Wavelength | | | |
| 214, 254 nm | | | |
| Compound, retention time, relative retention time | | | |
| Compound Name | Retention time (min) | RRT | |
| 15 | 5.48 | 0.64 | |

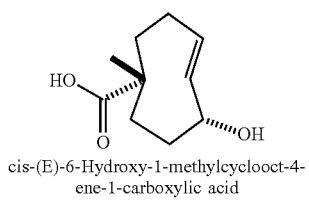

5.5 0.65 cis-(E)-6-Hydroxy-1-methylcyclooct-4-ene-1-carboxylic acid

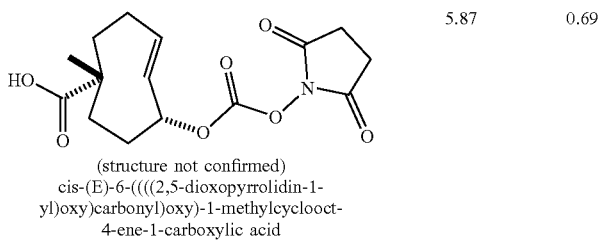

5.87 0.69

(structure not confirmed)
cis-(E)-6-((((2,5-dioxopyrrolidin-1-yl)oxy)carbonyl)oxy)-1-methylcyclooct-4-ene-1-carboxylic acid

| | Analytical Method: | | |
|---|---|---|---|
| 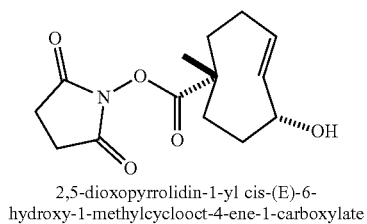<br>2,5-dioxopyrrolidin-1-yl cis-(E)-6-hydroxy-1-methylcyclooct-4-ene-1-carboxylate | | 7.07 | 0.83 |
| 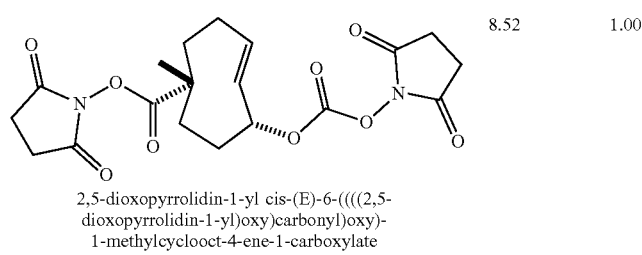<br>2,5-dioxopyrrolidin-1-yl cis-(E)-6-((((2,5-dioxopyrrolidin-1-yl)oxy)carbonyl)oxy)-1-methylcyclooct-4-ene-1-carboxylate | | 8.52 | 1.00 |

Example 4: Chiral Resolution of Compound VIIC

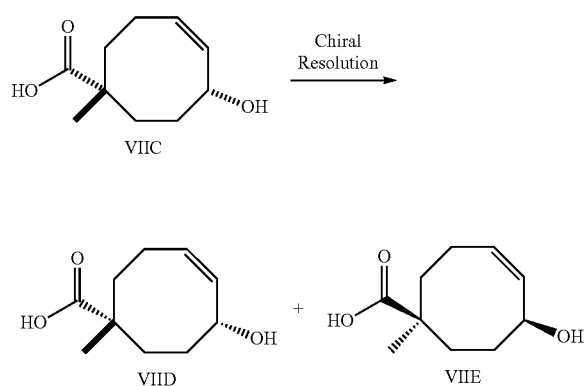

Resolution screening on compound VIIC was performed using each of the chiral bases (S)-2-amino-1-propanol (L-alaninol), (R)-(+)-1-phenylethylamine, L-(−)-2-amino-1-butanol, (1R,2S)-(−)-ephedrine, (S)-(+)-2-amino-3-methyl-1-butanol (L-valinol), (S)-(−)-N-benzyl-alpha-methylbenzylamine, (+)-dehydroabietylamine, (1S,2S)-(+)-2-amino-1-phenyl-1,3-propanediol, (R)-(+)-3-pyrrolidinol, (S)-(+)-2-pyrrolidinemethanol (L-prolinol), (S)-(−)-1-(1-naphthyl)ethylamine, (R)-1-amino-2-propanol, L-proline amide, (1R,2R)-(−)-pseudoephedrine, L-phenylalaninol, (1R,2R)-2-amino-1-(4-nitrophenyl)propane-1,3-diol, cinchonine, quinidine, quinine, cinchonidine, (S)-(+)-L-phenylglycinol, (R)-(−)-2-phenylglycine amide, (R)-(+)-2-phenylpropylamine, L-phenylalanine amide, (S)-diphenyl-2-pyrrolidine methanol, (1S,2S)-(+)-N-p-tosyl-1,2-diphenylethylenediamine, (1S,2R)-(+)-2-amino-1,2 diphenyl-ethanol, N-methyl-D-glucamine, (1S,2S)-(−)1,2-diphenylethylene diamine, (1R,2R)-diaminocyclohexane, (R)-(2-methoxyphenyl)ethylamine, (S)-p-chlorophenylethylamine, (R)-(+)-1-(4-methylphenyl)ethylamine, (S)-2-amino-1,1-diphenyl-1-propanol, (1S,2S)-(−)1,2-diphenylethylene diamine, and (1R,2R)-diaminocyclohexane, in each of the following solvents: water, acetonitrile, 1:1 water: ethanol, ethanol, IPA, MEK, iPrOAc, and dioxane. Select results of the resolution of compound VIIC on 100 mg scale, starting in 18 mL solvent are shown below.

| | Toluene | EtOAc | iPrOAc | TBME | Et$_2$O | acetone | MEK |
|---|---|---|---|---|---|---|---|
| R-1-Amino-2-propanol 1 eq | x | −2/48 | −7/37 | −8/52 | −3/54 | −62/65 | −7/48 |
| 0.5 eq | | | −48/58 | | | x | |
| 0.5 eq. + 0.5 eq NaOH | | | | | | x | |
| 0.5 eq. + 0.5 eq NaOH | | | | | | x | |
| R-Phenylglycinol 1 eq | x | x | 56/−75 | x | x | x | x |
| 0.5 eq. | | | 61/−42 | | | | |

1. 100 mg Compound VIIC and 44 mg R-aminopropanol in 18 mL iPrOAc: S=109 mg −7% ML=36 mg 37%.
2. 100 mg Compound VIIC and 22 mg R-aminopropanol in 18 mL iPrOAc: S=68 mg −48% ML=54 mg 58%.
3. 100 mg Compound VIIC and 81 mg R-phenylglycinol in 18 mL iPrOAc: S=79 mg 56% ML=98 mg −75%.
4. 100 mg Compound VIIC and 40 mg R-phenylglycinol in 18 mL iPrOAc: S=58 mg 61% ML=86 mg −42%.
5. 100 mg Compound VIIC and 150 mg L-diphenylpyrolidine methanol in 18 mL iPrOAc: S=167 mg 0% ML=50 mg 0%.
6. 100 mg Compound VIIC and 75 mg L-diphenylpyrolidine methanol in 18 mL iPrOAc: S=104 mg 0% ML=63 mg 0%.

Example 5: Chiral Resolution of (Z)-6-hydroxy-1-methylcyclooct-4-ene-1-carboxylic acid The following example shows the chiral resolution of (Z)-6-hydroxy-1-methylcyclooct-4-ene-1-carboxylic acid using (R)-2-amino-2-phenylethan-1-ol, which provides the opposite enantiomer of that provided by Example 2. The (−) sign is assigned to the % ee in order to distinguish between both of the enantiomers, and does not represent optical rotation.

(Z)-6-hydroxy-1-methylcyclooct-4-ene-1-carboxylic acid (8.00 g, 1 eq, 43.4 mmol) was dissolved in 900 isopropyl acetate at 68° C. in a 2 L three necked flask (some minor white insoluble material smeared onto the glass and remained there during the entire first step). (R)-2-amino-2-phenylethan-1-ol (5.96 g, 1 eq, 43.4 mmol) was added and the mixture was stirred with and overhead stirrer at 135 rpm.

The clear mixture was cooled at 10° C./hour and seeded upon every two degrees cooling, using seeding crystals with −61% ee. At 48° C. crystallization occurred. The mixture was further cooled to 35° C. at 10° C./hour and subsequently allowed to reach room temperature overnight.

Filtration gave 7.2 gram of solids with ee=−55% and 6.6 gram of material in the mother liquor with ee=83%.

6.2 gram of the solids obtained in step 1 were suspended in 255 mL isopropylacetate in a 1 L three necked flask and heated to 70° C. while stirring with an overhead stirrer at 135 rpm. After 5 minutes, the mixture was allowed to reach room temperature overnight. Filtration gave 5.1 gram of solids with ee=−76% and 1.0 gram of material in the mother liquor with ee=72%.

3.7 gram of the solids obtained in step 2 were suspended in 20 mL 2-butanone in a 100 mL round bottomed flask and heated to reflux while stirring with a magnetic stirrer. 12 mL methanol was added, after which the suspension became a clear solution. The mixture was allowed to reach room temperature overnight, during which it had crystallized. Filtration gave 2.0 gram of solids with ee=−92% and 1.7 gram of material in the mother liquor with ee=−71%.

1.0 gram of the solids obtained in step 3 were suspended in 10 mL isopropanol in a 100 mL round bottomed flask and heated to 60° C. while stirring with a magnetic stirrer. After 5 minutes, the mixture was allowed to reach room temperature overnight. Filtration gave 0.85 gram of solids with ee=−100% and 0.15 gram of material in the mother liquor with ee=−56%.

Example 6: Synthesis of trans-Cyclooctene (TCO)-doxorubicin Conjugate 12

Procedures to Compound 11:

Process for the synthesis of trans-cyclooctene (TCO)-doxorubicin conjugate 11 from TCO starting material 10 in 98% yield on the single gram-scale. Literature reference reports synthesis of 134 mg 11 in 68% yield. (Rossin, R. et al. *Bioconjugate Chem.* 2016, 1697-1706).

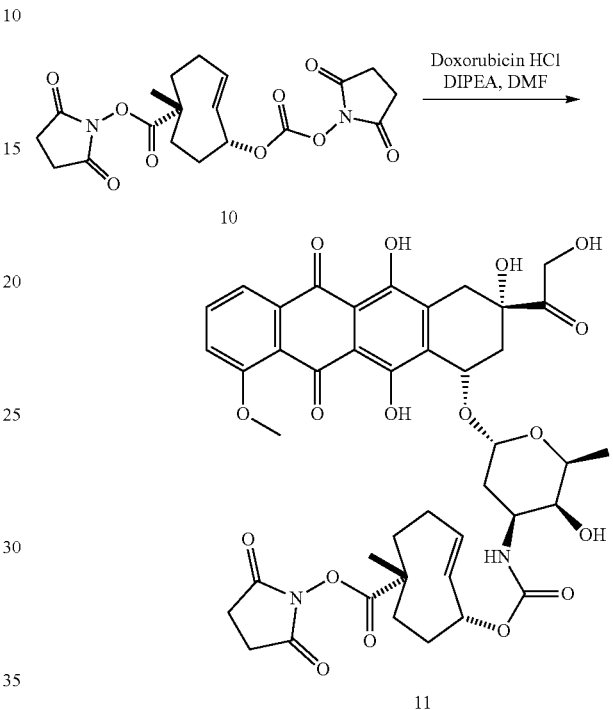

To a DMF (10 mL, 10 V) solution of Doxorubicin HCl (1.0 g, 1.72 mmol, 1.0 eq.) was added 10 (874.0 mg, 1.2 eq.) followed by adding DIPEA (0.9 mL, 3.0 eq.). The mixture was stirred at RT for 1.5 h, HPLC showed the formation of the product 11 (LCAP: 88.5%) and a small amount of Doxorubicin (LCAP: 0.3%). Assay yield of 11 was 102.6%. The reaction mixture was diluted with DCM (40 mL) and washed with water (total: 250 mL, HPLC monitored to make sure most DMF was washed out) and brine (10 mL). The DCM extracts were dried over $Na_2SO_4$ and concentrated to give crude residue. Isolated 1.7 g crude 11 (95.1% LCAP).

The residue was purified by silica gel chromatography to give 11 as a red solid. Isolated 1.44 g purified 11 (94.8% LCAP and 97.1% LCWP) in a 98.0% uncorrected yield. Neither 10 nor Doxorubicin were detected in the isolated material.

As the purity of 11 did not seem to improve significantly after silica gel purification, this step may not be necessary.

Procedures to Compound 12

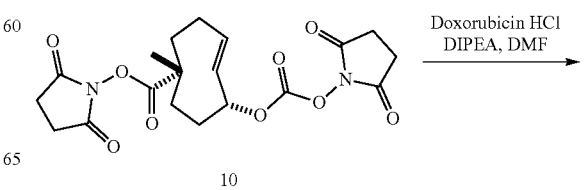

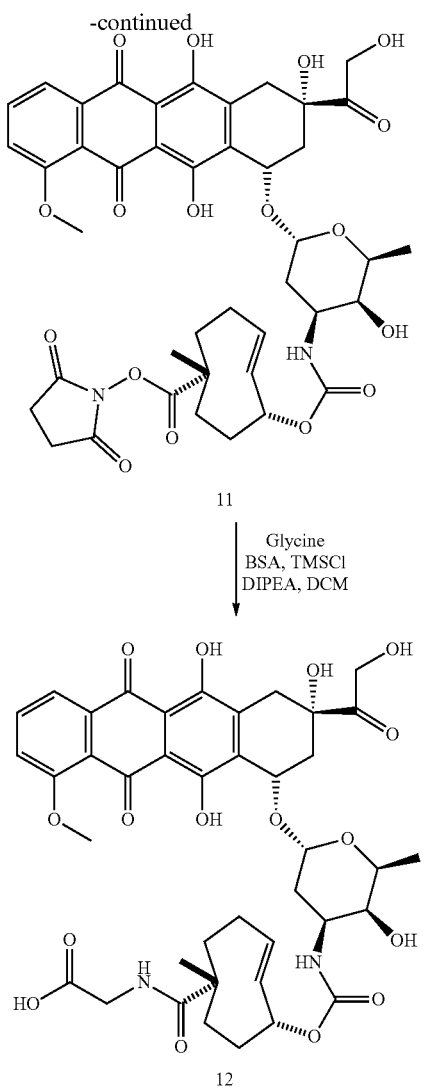

One-pot method for 10 to 12, 89% purity without chromatography: To a DMF (10 mL, 10 V) solution of Doxorubicin HCl (1.0 g, 1.72 mmol, 1.0 eq.) was added compound 10 (874.0 mg, 1.2 eq.), followed by adding DIPEA (0.9 mL, 3.0 eq.). The mixture was stirred at RT for 1.25 h, HPLC showed the formation of the product 11 (LCAP: 87.3%) and a small amount of Doxorubicin (LCAP: 0.4%). Assay yield is 95.2%. To the reaction mixture was added a suspension of glycine (1.29 g, 10.0 eq.), N,O-bis(trimethylsilyl)acetamide (BSA) (2.11 mL, 5.0 eq.), DIPEA (6.0 mL, 20.0 eq.) in DCM (20 mL). The resulting mixture was stirred at RT for 24 h. HPLC showed 87.7% LCAP for 12, 4.4% for 11.

The reaction mixture was filtered through a pad of Celite, washed with DCM (3 mL). The filtrate was concentrated to give a residue (4.9 g), which was mixed with water (26 mL) and added 4 mL 1 N NaOH to help dissolve the solid at 0° C. The mixture was then extracted with MTBE, but found emulsion was formed, more water (5 mL) and 1N NaOH (2 mL) and MTBE were added, eventually, two layers were formed, the aqueous layer (total volume: ~120 mL) was extracted with MTBE (3×60 mL) and then acidified with 1N HCl to pH=1-2.

The orange precipitate was collected by filtration and washed with water and dried under vacuum to give 1.25 g 12 (89.3% LCAP) in 89.2% uncorrected yield.

One-pot method for 10 to 12 with chromatography To a DMF (2.5 mL, 10 V) solution of Doxorubicin HCl (250 mg, 0.431 mmol, 1.0 eq.) was added compound 10 (218.5 mg, 1.2 eq.), followed by adding DIPEA (0.23 mL, 3.0 eq.). The mixture was stirred at RT for 3 h, HPLC showed the formation of the product 11 (LCAP: 91.8%) and a small amount Doxorubicin (LCAP: 0.3%). Assay yield is 92%. To the reaction mixture was added a preformed suspension of glycine (323.6 mg, 10 eq.), BSA (0.528 mL, 5 eq.) and DIPEA (1.5 mL, 20 eq.) in 5 mL DCM, which was stirred at RT for 2-3 h. The resulting mixture was stirred at RT for 25 h. After filtration and concentration, the residue was subjected to reverse phase ISCO. The collected fractions were lyophilized.

One-pot method for 10 to 12, alternative method—reverse order of addition: To a DMF (2.5 mL, 10 V) solution of Doxorubicin HCl (250 mg, 0.431 mmol, 1.0 eq.) was added compound 10 (218.5 mg, 1.2 eq.), followed by adding DIPEA (0.23 mL, 3.0 eq.). The mixture was stirred at RT for 1 h, HPLC showed the formation of the product 11 (LCAP: 88.8%) and a small amount Doxorubicin (LCAP: 0.5%). Assay yield is 93.3%. This reaction mixture was used directly as described below.

i) To a suspension of glycine (64.7 mg, 0.86 mmol, 10 eq.) in 1 mL DCM were added BSA (0.105 mL, 5 eq.) and DIPEA (0.30 mL, 20 eq.) at RT under nitrogen. The mixture was refluxed for 2 h, then cooled down to room temperature. To this was added reaction mixture for 11 (0.5 mL). The resulting mixture was heated at 40° C. for 5 h and monitored by HPLC. The reaction mixture was then cooled down to RT, filtered through a pad of Celite, washed with DCM. The filtrate was concentrated to give a residue (0.64 g), which was mixed with 0.2 N NaOH (0.5 mL) and the mixture was extracted with MTBE (2×1 mL). The aqueous layer was then acidified with 1 N HCl (0.2 mL) to pH=4-5. Gum-like precipitates were formed and collected, which showed 88.7% LCAP for 12. The aqueous is mainly a mixture of water with DMF.

ii) To a suspension of glycine (64.7 mg, 0.862 mmol, 10 eq.) in 1 mL DCM were added BSA (0.105 mL, 10 eq.) and DIPEA (0.30 mL, 40 eq.) at RT under nitrogen. The mixture was stirred at RT for 5 min, then reaction mixture[24-R174](0.5 mL) was added. The resulting mixture was stirred at RT for 22 h. HPLC showed 90.4% LCAP for 12, no other peak is >5% LCAP. The reaction mixture was filtered through a pad of Celite, washed with DCM. The filtrate was concentrated to give a residue, which was subjected to reverse phase ISCO purification. The collected fractions were lyophilized.

Comparative Synthesis: Conversion of 11 to 12 using TMSCl as protection reagent: To a suspension of glycine (89.3 mg, 1.19 mmol, 10 eq.) in 6 mL 60% $CHCl_3$/MeCN was added TMSCl (127.7 mg, 10 eq.) at RT under nitrogen. The mixture was refluxed for 2 h, then cooled down to room temperature. DIPEA (0.41 mL, 20 eq.) was added and followed by compound 11 (100.0 mg, 1.0 eq.). The resulting mixture was heated at 65° C. for 4.5 h and monitored by HPLC. The reaction was then diluted with water (10 mL) and extracted with DCM (3×25 mL). The DCM extracts were purified by silica gel chromatography to give compound 12 (7.3 mg, 24-165-2, LCAP for 12:78.8%). The aqueous layer was purified by reverse phase ISCO (0-50%

MeCN/water) to give 12 (19.6 mg, LCAP for 12:87.6%). Isolated (uncorrected) yield was 28.3%.

Compound-12-Na Formation

A 2000 mL flask was equipped with overhead stirrer, temperature probe, and nitrogen inlet/outlet. Acetone (5 vol., 128 mL) was charged to the flask and agitated at 20 to 25° C. under nitrogen. The crude compound 12 (25.6 g, 0.0315 moles, 1 equiv., the amount was from wt. assay %) was slurred with a part of acetone (7 volumes, 179 mL) and charged to the flask. The rest of the acetone was used to rinse the compound 12 free acid flask and charged to the 2000 mL flask. The mixture was purged briefly with nitrogen and then blanket under nitrogen.

To the stirring suspension, water (3.3 vol. 84.5 mL, degassed under vacuum to remove oxygen) was added in portions at 20 to 25° C. The mixture was completely dissolved (checked it with flush light).

NaHCO$_3$ (0.592 M, 5% in USP water, 53.3 mL, approximately 1 equiv., degassed under vacuum) was added in portions to the mixture under nitrogen at 20-25° C. with agitation. The mixture was filterable and stirred at 20 to 25° C. for approximately 30 min.

To the resulting solution in the 2000 mL flask, acetone (~35 vol. 896 mL) was added through in portions over ~10 min at 19 to 24° C. to form solid suspension. The mixture was stirred at 20-24° C. for ~30 min.

Agitation was stopped to allow solids set at bottom of the flask (over ~1 min). The mixture was filtered. The flask was rinsed with acetone (3×75 mL) and the rinse was used to wash the solid cake.

The wet solid was transferred into 500 mL round bottom flask and dried under vacuum at room temperature (20 to 25° C.) until a consistent weight was achieved.

Example 7: Synthesis of trans-Cyclooctene (TCO)-doxorubicin Conjugate 12-Ala

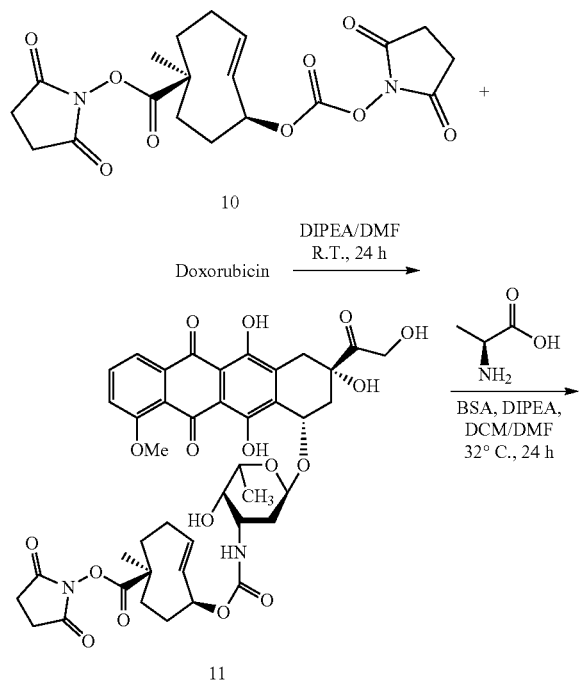

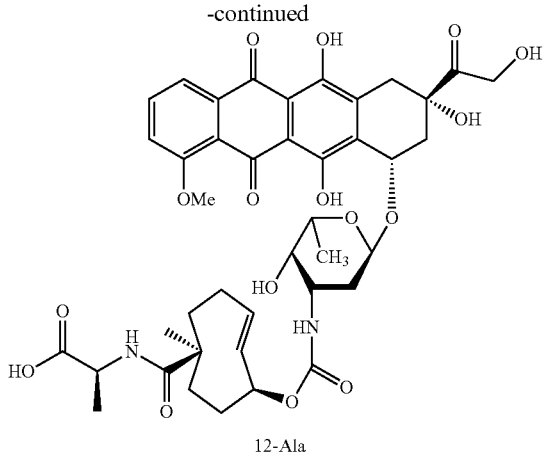

12-Ala

General Procedure for compound 11: Compound 10 (240 mg, 0.569 mmol, 1.0 eq) was dissolved in dry DMF (6 mL) followed by the addition of doxorubicin (395 mg, 0.683 mmol, 1.2 eq, HCl salt) and N,N-diisopropylethylamine (367 mg, 2.85 mmol, 5.0 eq). The solution was stirred overnight at r.t. under nitrogen and aluminum foil protection. The reaction mixture was diluted with DCM, washed with 5% aq citric acid, dH$_2$O, and brine. The organic layer was dried over Na$_2$SO$_4$ filtered and concentrated under reduced pressure to afford compound 11 (200 mg) as red solid.

TLC: DCM/methanol/acetic acid (20:1:0.2);

R$_f$ (Compound 11)=0.35;

LC-MS: 851.2 [M+H]$^+$;

General Procedure for 12-Ala: A mixture of L-alanine (52.6 mg, 0.59 mmol, 10 eq), BSA (60 mg, 0.294 mmol, 5.0 eq), DIPEA (152 mg, 1.18 mmol, 20.0 eq) in DCM (0.5 mL) was stirred for 30 min, and added to a solution of compound 11 (50.0 mg, 0.059 mmol, 1.0 eq) in DMF (0.2 mL). The reaction mixture was heated at 32° C. overnight under nitrogen and aluminum foil protection. The reaction mixture was concentrated to dryness and the residue was diluted with acetonitrile (2 mL). The resulting crude reaction mixture was purified by prep-HPLC (5% to 100% CH$_3$CN in 30 minutes, neutral, pH 7) to give 12-Ala (2.3 mg) after the fractions with desired mass were lyophilized to dryness. LC-MS: 846.8 [M+H]+, 822.5 [M−H]$^-$; $^1$H NMR (300 MHz, CD$_3$OD): δ 7.85 (m, 1H), 7.78 (m, 1H), 7.52 (m, 1H), 5.64 (m, 1H), 5.40 (m, 2H), 5.07 (m, 2H), 4.74 (s, 1H), 4.24 (m, 2H), 3.82 (s, 3H), 3.82 (m, 1H), 3.61 (m, 2H), 2.98 (m, 2H), 2.90 (m, 2H), 2.38-1.74 (m, 10H), 1.33 (d, J=6.3 Hz, 3H), 1.26 (d, J=6.3 Hz, 3H), 1.09 (s, 3H).

Example 8: Comparative Examples

Evaluation of alternate synthetic approaches to trans-cyclooctene (TCO)-doxorubicin conjugate (Dox-TCO-Gly). Direct Coupling of Glycine to Dox-TCO-NHS (without Protecting Groups) is Inefficient

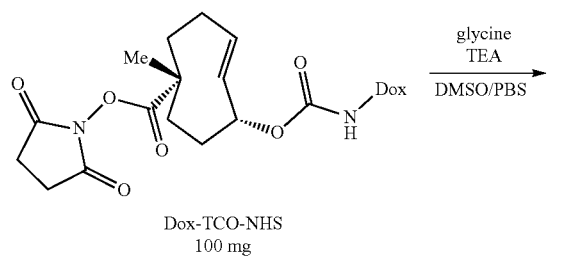

TMS protection route

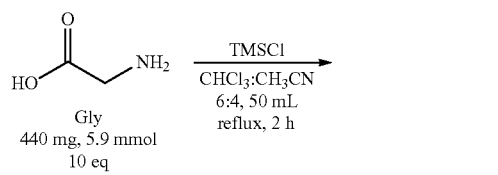

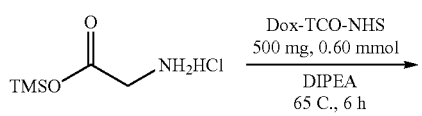

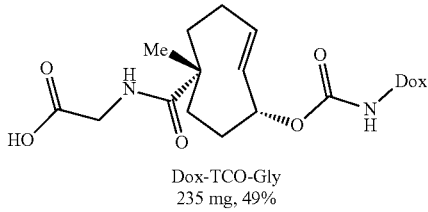

To a suspension of glycine (440 mg, 5.9 mmol, 10 equiv) in 50 mL of $CHCl_3$:MeCN (60%: 40%) was added TMSCl (638 mg, 5.9 mmol, 10 equiv) in one portion. The resulting mixture was stirred at reflux (80 C) for 2 h and then cooled to room temperature. DIPEA (2 mL, 12 mmol, 20 equiv) and Dox-TCO-NHS (500 mg, 0.58 mmol) were added at room temperature and the mixture was then stirred at 65 C for 6 h. Analysis of crude HPLC indicated 78% yield. After removal of the solvents, the residue was dissolved in 5 mL water and purified by reversed phase chromatography (MeCN:water, 0→50%) to afford Dox-TCO-Gly (235 mg, 49%) as an orange solid.

Alternate Activating Group: PNP Results in Lower Dox Coupling Yield Compared to NHS

PNP 53%

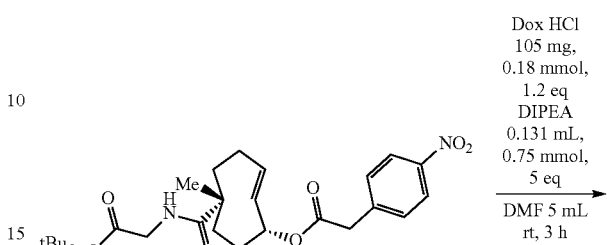

NHS - 72%

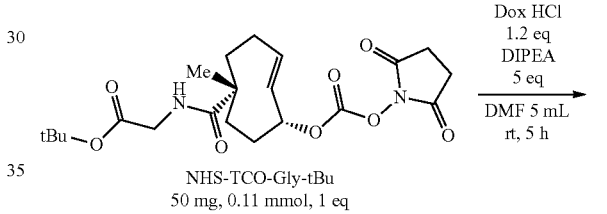

Alternate Protecting Group: Fmoc route - 4 steps, 17% overall

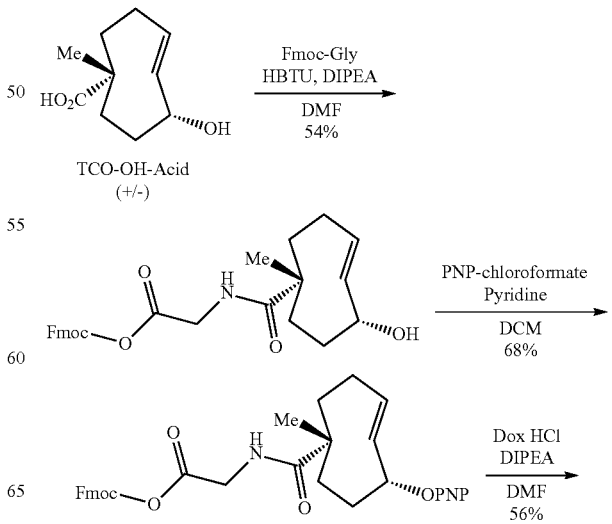

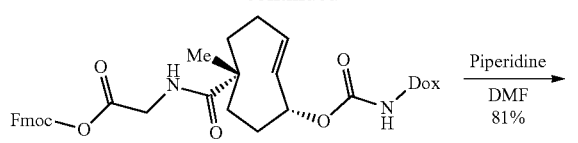

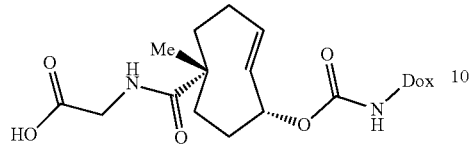

Alternate Protecting Group: tBu route - 4 steps, desired product not obtained

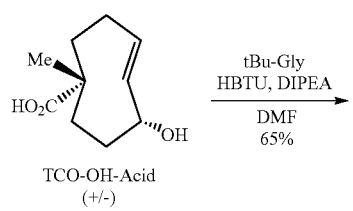

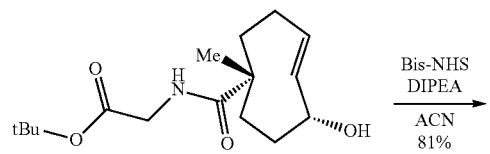

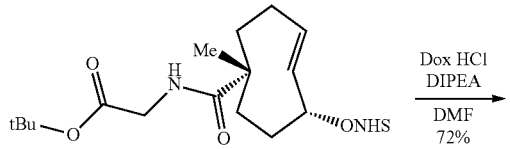

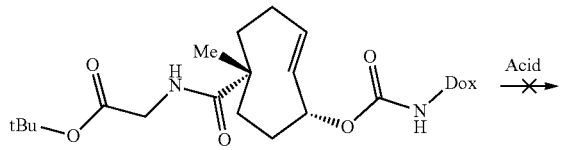

Various acidic deprotection conditions screened (e.g. TFA, AcOH, HCl, H₃PO₂) in different solvents—desired product never observed. By mass, always observe deprotection along with addition of water (possibly to Dox glycosidic bond or TCO alkene).

Direct Alcohol Monoactivation of TCO—Carboxylic Acid Activation Favored

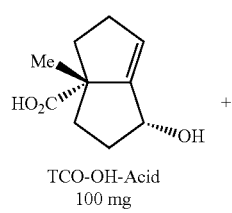

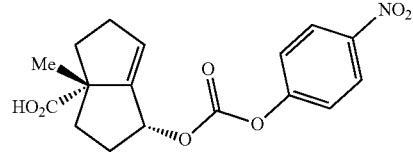

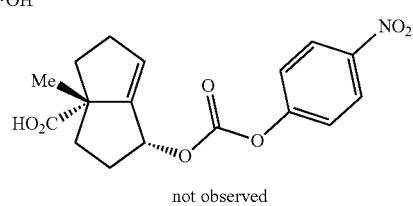

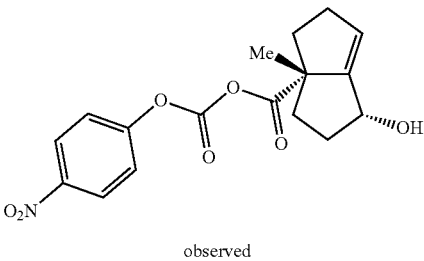

Alternate routes to alcohol activation—less efficient than NHS bis-activation route Alternate Route 1

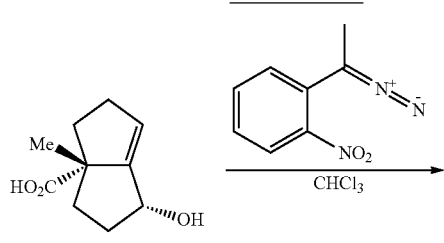

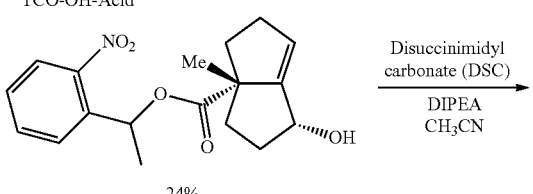

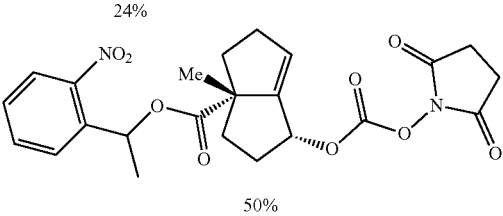

-continued

Alternate Route 2

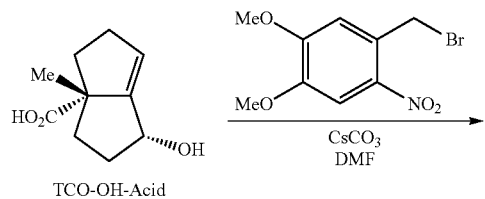

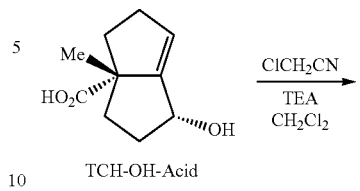

Alternate Route 3

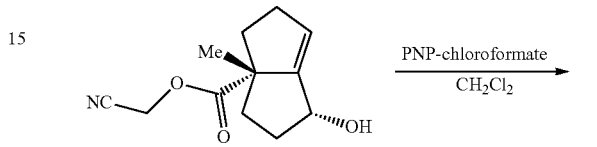

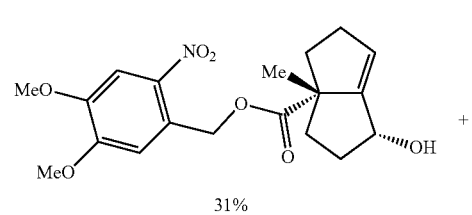

31%

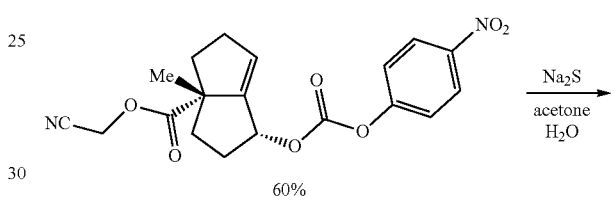

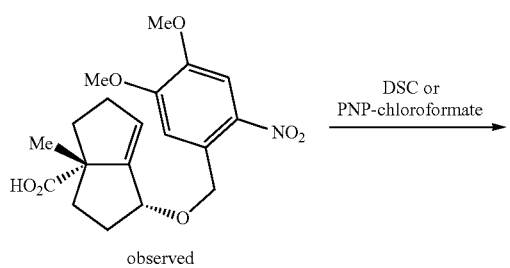

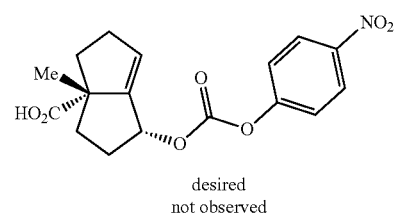

desired
not observed

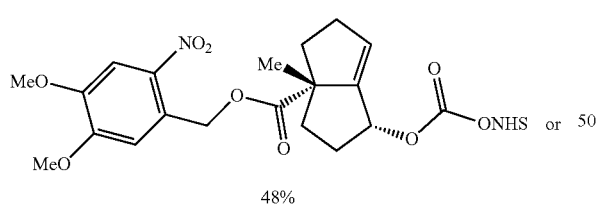

48%

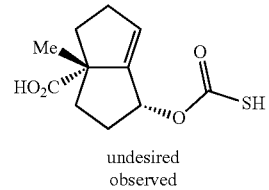

undesired
observed

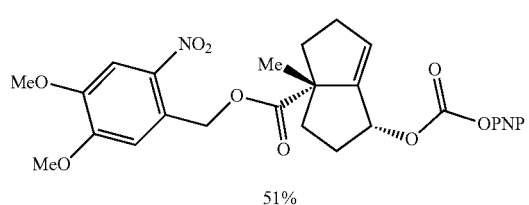

51%

Example 9: Pexidartinib-TCO-Glycine Conjugate Via BSA-Protection Method

This example provides methods for the conjugation of a TCO starting material, such as those described herein (e.g., compound 10) to Pexidartinib. Further modification of compound 15 with an amino acid moiety (e.g., glycine) is contemplated.

To a solution of compound 13 (418 mg, 1.0 mmol) in DMF (10 mL) at 0° C. was added NaH (ca. 60%, 44 mg, 1.1 mmol). The reaction mixture was stirred under $N_2$ for 1 h before Bis-NHS-TCO (398 mg, 1.0 mmol) was added. The resulting mixture was stirred at room temperature for 18 h. The reaction was quenched with water (10 mL). The product was extracted with ethyl acetate (2×40 mL). The combined organic layers were washed with water (4×15 mL), and brine (15 mL), dried ($MgSO_4$) and evaporated in vacuo. The product was purified by flash chromatography on silica gel eluting with EA/Hex (0%-100%) to give the intermediate 14 (463 mg, 64%) as a white solid. LCMS: $R_t$=1.281, m/z 725 [M+1]$^+$ To a solution of N-hydroxylsuccinimide ester 14 (200 mg, 0.28 mmol) and DMF (1.6 mL) were added into a solution of glycine (207 mg, 2.8 mmol), N,O-bis(trimethylsilyl) acetamide (285 mg, 1.4 mmol) and DIPEA (724 mg, 5.6 mmol) in DCM (3.2 mL). The resulting mixture was allowed to stir at room temperature for 16 h. The reaction was monitored by LCMS and HPLC to indicate the majority (68%) content was the desired product compound 15 (m/z 684.8(+) and 682.5(−), MW: 685.1). The reaction mixture was diluted with DCM (10 mL), and then filtered through a pad of Celite. The filtrate was concentrated to dryness. The residue was purified by Prep-HPLC (0.1% formic acid as buffer) to afford compound 15 (116.2 mg, 61%) as a white solid. LCMS: $R_t$=1.013, m/z 685 [M+1]$^+$ and 1368 [2M+1]$^+$.
$^1$H NMR (300 MHz, CHCl$_3$) δ 8.61 (s, 1H), 8.46 (d, J=1.8 Hz, 1H), 7.94-7.80 (m, 2H), 7.68-7.60 (m, 2H), 7.57 (s, 1H), 7.50 (dd, J=8.7 and 1.8 Hz, 1H), 6.50 (d, J=9.0 Hz, 1H), 6.34-6.16 (m, 2H), 5.66 (dd, J=16.2 and 2.4 Hz, 1H), 5.57 (s, 1H), 4.59 (s, 2H), 3.92-3.80 (m, 4H), 2.38-1.80 (m, 7H), 1.74-1.68 (m, 1H), 1.17 (s, 3H).

Example 10: Etoposide-TCO Conjugate

This example provides methods for the conjugation of a TCO starting material, such as those described herein (e.g., compound 10) to Etoposide.

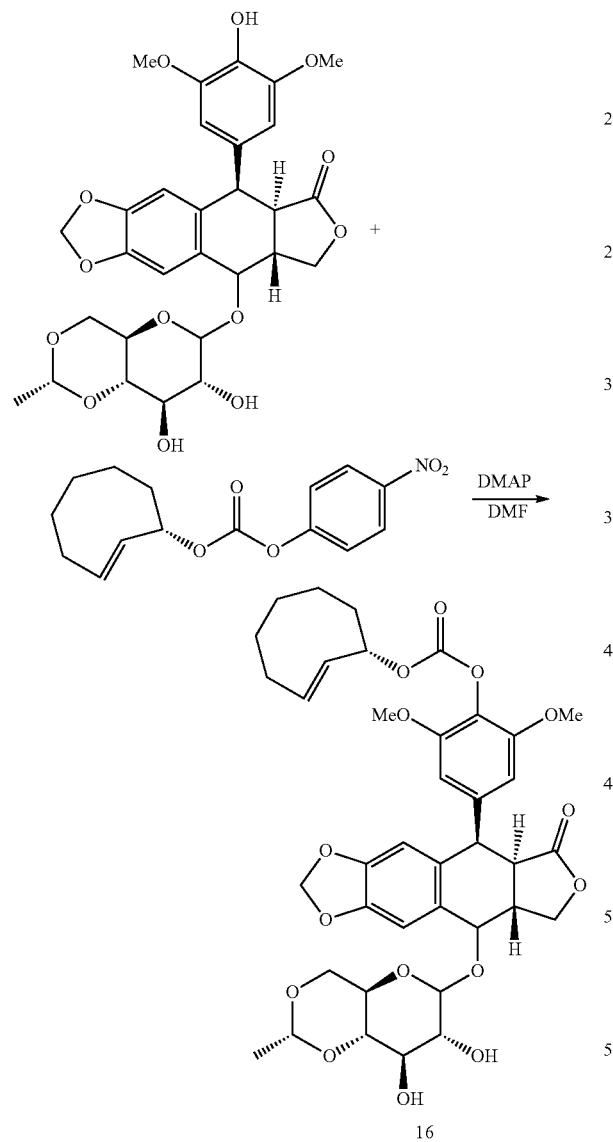

To a solution of etoposide (50 mg, 0.08 mmol) in DMF 5 mL, TCO-PNP (30 mg, 0.10 mmol) and DMAP (21 mg, 0.16 mmol) were added. The mixture was stirred for 3 days, and quenched with 20 mL water. The mixture was extracted with EtOAc (3×30 mL) and the combined organic phase was dried and concentrated. The residue was purified on column to give etoposide-TCO compound 16 (30 mg, 54%/). $^1$H NMR (500 MHz, CDCl$_3$) δ 6.84 (s, 1H), 6.53 (s, 1H), 6.27 (s, 2H), 6.03-5.85 (m, 3H), 5.51 (dd, J=16.5, 1.7 Hz, 1H), 5.33 (s, 1H), 4.92 (d, J=3.4 Hz, 1H), 4.74 (q, J=5.0 Hz, 1H), 4.60 (dd, J=15.7, 6.4 Hz, 2H), 4.42 (dd, J=26.1, 16.7 Hz, 1H), 4.29-4.12 (m, 2H), 3.68 (s, 6H), 3.62 (dd, J=17.9, 9.1 Hz, 1H), 3.59-3.52 (m, 1H), 3.41-3.36 (m, 1H), 3.37-3.22 (m, 5H), 2.86 (tdd, J=10.9, 8.0, 3.3 Hz, 1H), 2.49 (d, J=10.3 Hz, 1H), 2.19 (t, J=11.9 Hz, 1H), 2.08-1.94 (m, 2H), 1.89 (dt, J=15.1, 6.4 Hz, 1H), 1.68 (ddd, J=19.0, 15.3, 9.7 Hz, 2H), 1.59-1.46 (m, 1H), 1.38 (d, J=5.0 Hz, 3H), 1.22-1.10 (m, 1H), 0.81 (td, J=14.6, 5.6 Hz, 1H).

Example 11: Aniline Mustard-TCO Conjugate

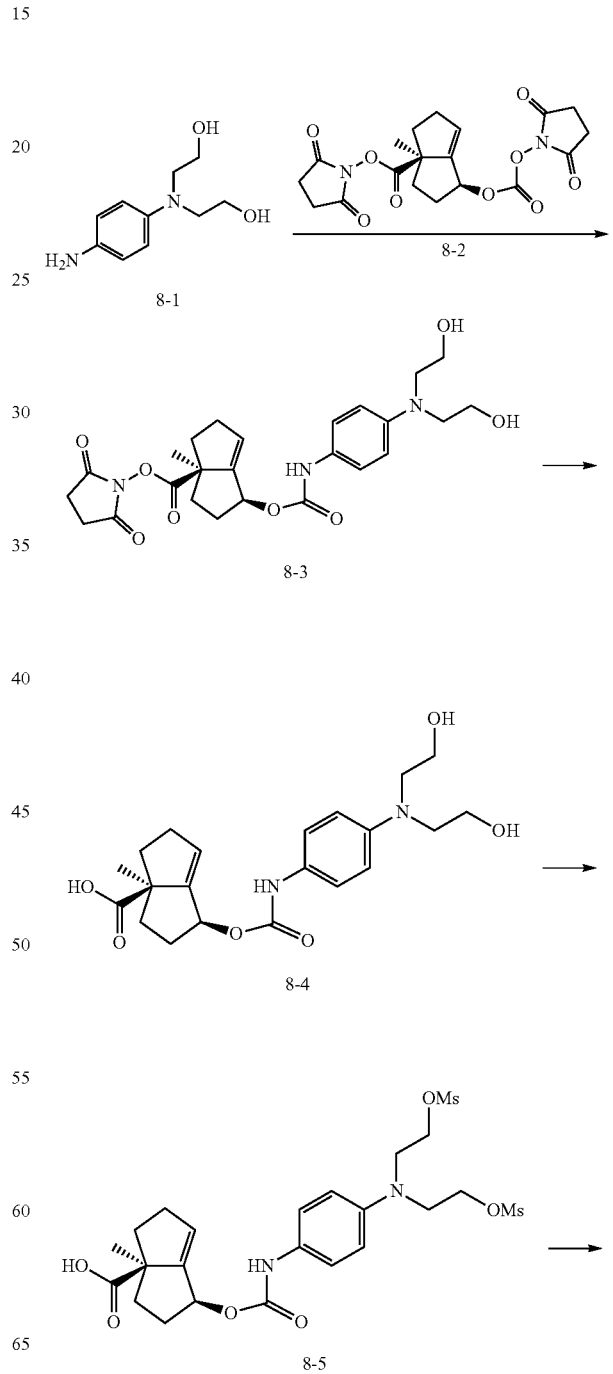

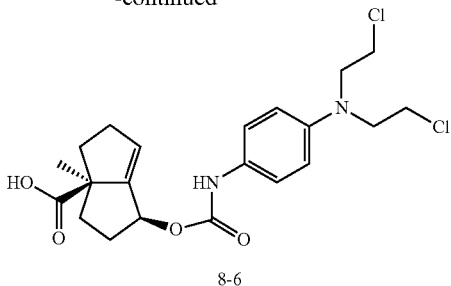

8-6

To a solution of 8-1 (212 mg, 0.72 mmol) in DMF (3 mL) was added 8-2 (305 mg, 0.72 mmol) and DIEA (279 mg, 2.17 mmol). The solution was stirred at rt overnight. After removal of solvent, DCM (30 mL) was added. The organics were washed with saturated NaHCO$_3$ (40 mL), water (30 mL), brine (20 mL), dried over Na$_2$SO$_4$, and concentrated to give a residue. The residue was triturated with ether (2×5 mL) and dried to give compound 8-3 (310 mg, 86%) as pale yellow solid.

To a solution of 8-3 (310 mg, 0.62 mmol) in THF (4 mL) and H$_2$O (1 mL) was added LiOH·H$_2$O (77 mg, 1.86 mmol) and DIEA (279 mg, 2.17 mmol). The solution was stirred at rt overnight. After removal of solvent, the residue was purified by prep-HPLC (water and ACN, 0.1% formic acid) to give compound 8-4 (140 mg, 56%).

To a solution of 8-4 (140 mg, 0.34 mmol) in DCM (4 mL) was added TEA (172 mg, 1.72 mmol) and MsCl (79 mg, 0.85 mmol). The solution was stirred at rt for 4 h. DCM (10 mL) was added. The organics were washed with water (2×10 mL), brine (10 mL), dried over Na$_2$SO$_4$, and concentrated. The residue was dried under high vacuum to give crude 8-5 (171 mg).

To a solution of 8-5 (170 mg, 0.3 mmol) in DMF (2 mL) was added LiCl (252 mg, 6.0 mmol). The mixture was stirred for 2 h at rt and then 60° C. overnight. After removal of solvent, DCM (10 mL) was added. The organic layer was washed with water (10 mL), brine (10 mL), dried over Na$_2$SO$_4$, and concentrated to give a residue. The residue was purified by prep-HPLC (water and ACN, 0.1% formic acid) to give compound 8-6 (86 mg, 64% in two steps) as off-white powder. LCMS: 443 [M+H]$^+$. $^1$H NMR (300 MHz, CD$_3$OD) δ 7.25 (d, J=7.8 Hz, 2H), 6.72 (d, J=7.8 Hz, 2H), 6.00 (m, 1H), 5.71 (m, 1H), 5.18 (s, 1H), 3.71-3.61 (m, 8H), 2.27-1.67 (m, 8H), 1.28 (s, 1H), 1.12 (s, 3H).

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure.

This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:

1. A process of preparing a compound of formula I, or a salt thereof:

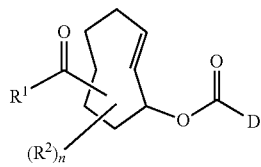

I wherein
R$^1$ is selected from the group consisting of —OR$^4$, optionally substituted heterocyclyl, and an amino acid moiety;
n is 0, 1, 2, 3, or 4;
each R$^2$ is independently C$_{1-4}$alkyl, C$_{1-4}$haloalkyl, and C$_{1-4}$alkoxy;
D is a payload moiety; and
R$^4$ is hydrogen or C$_{1-4}$alkyl;
comprising contacting a compound of formula II:

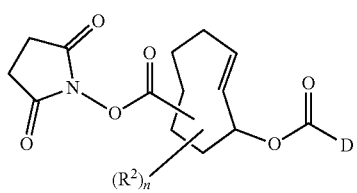

II with HO—R⁴, an optionally substituted heterocycle, or an amino acid moiety, or a salt thereof, and N,O-bis(trimethylsilyl)acetamide in an organic solvent in the presence of a base;

wherein the amino acid moiety is selected from the group consisting of a natural amino acid, an unnatural amino acid, —NR$^{1c}$—C$_{1-4}$alkylene-optionally substituted heterocyclyl, —NR$^{1c}$—C$_{1-4}$alkylene-N(R$^{1d}$)$_2$, —N(R$^{1c}$)CHR$^{1e}$CO$_2$H, —N(R$^{1c}$)—C$_{1-6}$alkylene-CO$_2$H, —N(R$^{1f}$)—C$_{2-4}$alkylene-(N(C$_{1-4}$alkylene-CO$_2$H)—C$_{2-4}$alkylene)$_m$-N(C$_{1-4}$alkylene-CO$_2$H)$_2$, —N(R$^{1e}$)CHR$^{1e}$C(O)OC$_{1-6}$alkyl, —N(R$^{1c}$)—C$_{1-6}$alkylene-C(O)O—C$_{1-6}$alkyl, and —N(R$^{1f}$)—C$_{2-4}$alkylene-(N(C$_{1-4}$alkylene-C(O)OC$_{1-6}$alkyl)-C$_{2-4}$alkylene)$_m$-N(C$_{1-4}$alkylene-C(O)OC$_{1-6}$alkyl)$_2$; wherein R$^{1c}$ and R$^{1d}$ are each independently hydrogen or C$_{1-4}$alkyl;

R$^{1e}$ is —C$_{1-4}$alkylene-CO$_2$H, —C$_{1-4}$alkylene-CONH$_2$, or —C$_{1-4}$alkylene-OH;

R$^{1f}$ is hydrogen, —C$_{1-6}$alkyl, or —C$_{1-4}$alkylene-CO$_2$H; and m is 0, 1, 2, or 3.

2. The process of claim 1, wherein the payload moiety is an anthracycline moiety, an auristatin moiety, a glycopeptide antibiotic moiety, or a lipopeptide antibiotic moiety.

3. The process of claim 2, wherein the payload moiety is a doxorubicin moiety, daunorubicin moiety, monomethyl auristatin E moiety, vancomycin moiety, or daptomycin moiety.

4. The process of claim 1, wherein R$^1$ is a natural amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; or an alanine moiety or a glycine moiety.

5. The process of claim 1, wherein the compound of formula I is represented by formula IA:

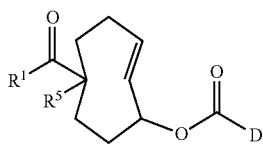

IA wherein

R$^1$ is selected from the group consisting of —OR⁴, optionally substituted heterocyclyl, and an amino acid moiety selected from the group consisting of —NR$^{1c}$—C$_{1-4}$alkylene-optionally substituted heterocyclyl, —NR$^{1c}$—C$_{1-4}$alkylene-N(R$^{1d}$)$_2$, —N(R$^{1c}$)CHR$^{1e}$CO$_2$H, —N(R$^{1c}$)—C$_{1-6}$alkylene-CO$_2$H, —N(R$^{1f}$)—C$_{2-4}$alkylene-(N(C$_{1-4}$alkylene-CO$_2$H)—C$_{2-4}$alkylene)$_m$-N(C$_{1-4}$alkylene-CO$_2$H)$_2$, —N(R$^{1e}$)CHR$^{1e}$C(O)OC$_{1-6}$alkyl, —N(R$^{1c}$)—C$_{1-6}$alkylene-C(O)O—C$_{1-6}$alkyl, and —N(R$^{1f}$)—C$_{2-4}$alkylene-(N(C$_{1-4}$alkylene-C(O)OC$_{1-6}$alkyl)-C$_{2-4}$alkylene)$_m$-N(C$_{1-4}$alkylene-C(O)OC$_{1-6}$alkyl)$_2$; wherein R$^{1c}$ and R$^{1d}$ are each independently hydrogen or C$_{1-4}$alkyl;

R$^{10}$ is —C$_{1-4}$alkylene-CO$_2$H, —C$_{1-4}$alkylene-CONH$_2$, or —C$_{1-4}$alkylene-OH;

R$^{1f}$ is hydrogen, —C$_{1-6}$alkyl, or —C$_{1-4}$alkylene-CO$_2$H; and m is 0, 1, 2, or 3;

R⁴ is hydrogen or C$_{1-4}$alkyl;

R⁵ is hydrogen or C$_{1-4}$alkyl; and

D is a payload moiety;

and the compound of formula II is represented by formula IIA:

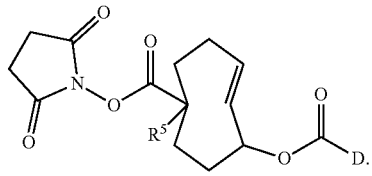

IIA

6. The process of claim 1, further comprising preparing the compound of formula II by reacting a compound of formula IV:

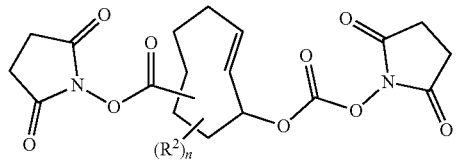

IV with a payload moiety, or a salt thereof, in an organic solvent in the presence of a base.

7. The process of claim 5, wherein the compound of formula IV is represented by formula IVA:

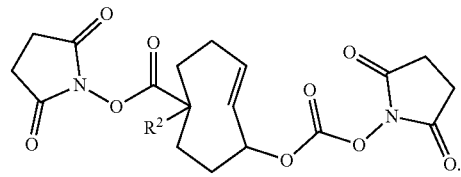

IVA

* * * * *